United States Patent [19]
Huie et al.

[11] Patent Number: 5,470,967
[45] Date of Patent: Nov. 28, 1995

[54] OLIGONUCLEOTIDE ANALOGS WITH SULFAMATE LINKAGES

[75] Inventors: Edward M. Huie; George L. Trainor, both of Wilmington, Del.

[73] Assignee: The Dupont Merck Pharmaceutical Company, Wilmington, Del.

[21] Appl. No.: 507,693

[22] Filed: Apr. 10, 1990

[51] Int. Cl.$^6$ ............................ C07H 21/00; C07H 21/04
[52] U.S. Cl. ...................... 536/24.3; 536/22.1; 536/23.1; 536/24.5
[58] Field of Search ................... 536/27, 28, 29, 536/23.1, 24.5, 22.1, 24.3

[56] References Cited

U.S. PATENT DOCUMENTS

| | | | |
|---|---|---|---|
| 3,622,561 | 11/1971 | Robins et al. | 536/27.3 |
| 3,687,808 | 8/1972 | Merigan, Jr. et al. | 536/24.5 |
| 4,469,863 | 9/1984 | Ts'o et al. | 536/24.5 |

FOREIGN PATENT DOCUMENTS

| | | |
|---|---|---|
| 89/03863 | 5/1989 | WIPO. |
| 89/11486 | 11/1989 | WIPO. |
| 89/120060 | 12/1989 | WIPO. |

OTHER PUBLICATIONS

Nuc. Acids Res. No. 9 (1981) Jäger et al. pp. 149–152.
J. Org. Chem. 49 2314–2317 (1984) Nelson et al.
Principles of Biochemistry, Lehringer pp. 799–800 (1986).
PNAS vol. 84 pp. 7706–7710 (1987) Matsukura et al.
Isono et al., *J. Antibiotics,* vol. 37, No. 6, pp. 670–672 (1984).
Ubukata et al., *Tet. Lett.* vol. 27, No. 33, pp. 3907–3908 (1986).
Shuman et al., *J. Am. Chem. Soc.,* vol. 91, No. 12, pp. 3391–3392 (1969).
Miller et al., *Annual Rep. Med. Chem.,* vol. 23, pp. 295–304 (1988).
Zon, *Pharm. Res.,* vol., 5, No. 9, pp. 539–549 (1988).

*Primary Examiner*—Douglas W. Robinson
*Assistant Examiner*—Gary L. Kunz
*Attorney, Agent, or Firm*—Blair Q. Ferguson

[57] ABSTRACT

Oligonucleotides possessing at least one sulfamate or sulfamide internucleotides linkages. These compounds can be used as specific hybridization probes to detect complementary nucleic acid sequences.

24 Claims, 4 Drawing Sheets

OLIGONUCLEOTIDE ANALOGS WITH SULFAMATE LINKAGES

FIELD OF THE INVENTION

This invention relates to novel compounds in which one or more of the internucleotide phosphodiester linkages in oligonucleotide analogs have been replaced by a sulfur based linkage.

BACKGROUND OF THE INVENTION

The repertoire of substances available for therapeutic purposes consists primarily of relatively low-molecular weight organic compounds. Recently, the repertoire has been expanded to include proteinaceous materials which have been engineered for efficacy, specificity and stability. Increasing attention is now being focused on the therapeutic potential of other classes of biomacromolecules, including nucleic acids.

Nucleic acids are linear phosphopentose polymers bearing pendant adenine (A), guanine (G), cytosine (C), and thymine (T) [or the related uracil (U)] base groups. The pentose may be ribose (RNA) or 2'deoxyribose (DNA). They are attractive candidates for therapeutics due to the high potential for selectivity. The basis for this high selectivity is the well-known ability of a nucleic acid to form an antiparallel, two-stranded, helical structure (or duplex) with its structural complement through the formation of hydrogen bonds between the bases on opposite strands (Watson-Crick base pairs). Complementarity is defined as the pairing of G with C and A with T [or U] on opposite strands. Duplexes with perfect complementarity are thermodynamically preferred. For short [<20 residues or nucleotides (nt)] oligonucleotides, a single improper pairing or mismatch can significantly destabilize the duplex. Thus one can, in principle, selectively address a single site in a $3 \times 10^9$ nt human genome (the genetic material of a human in its entirety) with an oligonucleotide of 16–20 nt. This is substantially greater selectivity than one can generally achieve with traditional, low-molecular weight agents. With this degree of potential selectivity, one can consider the approach of exerting a therapeutic effect at the level of gene expression. For viral agents which act through integration of their genetic material into the host system, one can envision blocking one of the many steps involved in integration and replication.

Most of the attempts to use nucleic acids as complementary addressed therapeutic agents have involved single-stranded targets. Such targets include messenger RNA (mRNA) and single-stranded viral genomes. In such cases, the reagent nucleic acids are complementary to the target and are referred to as "anti-sense reagents". The process of using such agents to exert a specific effect is referred to herein as "anti-sense targeting"[1-3,32].

More recently, a second, high-specificity mode of nucleic acid binding has been investigated. It has been found that certain sequences of duplex DNA will bind a third strand to form a triple helix or triplex[4]. Triplex formation involves the formation of base triples with the additional base forming hydrogen bonds in the so-called Hoogsteen mode. Reagents designed to bind in such a mode are referred to herein as "triplex reagents" and the process of using such reagents to exert a specific effect will be referred to as "triplex targeting". The advantage of the triplex targeting approach is that one can address double-stranded genomic DNA directly. The disadvantage is that, at least at this time, not all sequences can be addressed in this fashion.

The ease of synthesis and chemical stability of simple, unmodified oligodeoxynucleotides has led to widespread investigation of their use as anti-sense reagents. This approach has been used with varying degrees of success in vitro against human immunodeficiency virus (HIV), Rous sarcoma virus, and c-myc oncogene expression, among others.[28]

Simple oligodeoxynucleotide anti-sense reagents may exert their effects in one or both of two ways. They can simply bind their target through duplex formation thereby reducing the available concentration of functional single-stranded target. Alternatively, in the case where the target is a single-stranded RNA, the RNA/DNA hybrid may Serve as a substrate for endogenous ribonuclease H (RNaseH). RNaseH is an enzyme which will cleave the RNA strand of an RNA/DNA hybrid through phosphodiester bond hydrolysis. The mediation of RNaseH can allow anti-sense reagents to operate at concentrations well below those required to drive all of the target to hybrid since the reagent itself is not cleaved and each molecule can direct the cleavage of many molecules of target.

A number of structural modification approaches to improve the function of oligodeoxynucleotides as anti-sense reagents have been investigated. One class of modification involves the attachment of chemical appendages to the reagent to stabilize the reagent/target duplex or cleave the target at the site of attachment. Acridine derivatives attached via flexible tethers have been shown to improve the thermodynamic stability of the duplex through intercalation[5]. Similarly, oligodeoxynucleotides bearing tethered psoralens can be covalently cross-linked to target following irradiation of the duplex[6]. Cross-linking can also be accomplished through the use of tethered alkylating agents[7]. Cleavage of the target through the use of oligodeoxynucleotides bearing tethered ethylenediaminetetraacetic acid (EDTA)/iron[8] or 1,10-phenanthroline/copper[9] has been demonstrated in vitro. Numerous other attachments for these purposes have been described. Functionalization with poly (L-lysine) has been employed to improve transport.[31]

The use of oligodeoxynucleotides as anti-sense reagents in vivo is hampered, however, by two fundamental problems. The first problem is that small single-stranded oligodeoxynucleotides are rapidly digested by endogenous nucleases. As a result high in vivo concentrations are difficult to sustain. The second problem is that oligodeoxynucleotides are highly charged having roughly one full negative charge per nucleotide residue. This generally results in a reduced rate of transport across membranes which in some cases limits the access to the ultimate site of action. These two effects combine to afford relatively low bioavailability.

The attachment of chemical functionalities (as described above) to the terminii of oligodeoxynucleotides can provide enhanced nuclease-resistance in some cases. Alpha-Oligodeoxynucleotides, in which the attachment of the base to the ribofuranosyl ring has been changed from beta- to alpha-, form parallel stranded duplexes and show increased nuclease resistance[10].

In several approaches to solve the stability and transport problems, the central phosphorus atom in the linkage has been retained but attached atoms have been replaced or modified. O-Alkylphosphotriesters are uncharged but are more bulky than the natural linkage and show somewhat reduced chemical stability[11,12]. Phosphorothioate diesters are isostructural with the natural linkage and show increased resistance to nucleases but are still charged[13]. Methylphosphonates are uncharged and considerably more lipophilic but fully replaced hybrids are not substrates of RNaseH[14].

One fundamental difficulty with these analogues is the fact that all derive from a single replacement of one of the non-bridging oxygen atoms on the phosphodiester linkage. Since that phosphorus is prochiral within the linkage, non-specific replacement of one oxygen results in the formation of a chiral center and hence a pair of diastereomers. Each additional non-specific replacement doubles the number of diastereomers present. These diastereomers have differing physical properties complicating analysis and in some cases have been shown to have widely differing abilities to form hybrids[34]. Thus oligodeoxynucleotide analogues with multiple linkage replacements are generally complex mixtures of species which can have widely differing biological efficacy.

The diastereomer mixture problem can be circumvented by replacement of both bridging oxygens in the phosphodiester linkage with the same chemical group. Along these lines, phosphorodithioate diesters have been investigated[15]. However, like the phosphorothioate linkage, this moiety is still charged.

Approaches involving more extensive modifications have also been reported. Replacement of the phosphodiester linkage with a carbon centered, neutral carbamate have been investigated[16,17]. The planarity of the carbamate linkage ensures that its introduction does not generate diastereomers but it represents a departure from tetrahedral geometry of the phosphodiester with consequences that have not been fully explored. At least one derivative has been shown to be able to form duplex with complementary target. The carbamate's nuclease sensitivity and ability to activate RNaseH have not yet been reported on.

Several recent studies have focused on oligodeoxynucleotides with partial phosphodiester linkage replacement. The rationale here is that one may be able to engineer a balanced profile of desirable properties (e.g., nuclease resistance, hybrid stability, RNaseH activation, etc.). These studies while useful are unlikely to lead to a general solution to the problems listed above.

With some analogues, the situation is further complicated by the observation that biological effects are being exerted in a non-sequence-specific manner[18,19]. The origins of these effects remain obscure.

The described list of modifications explored in attempts to enhance the function of oligodeoxynucleotides as anti-sense reagents is representative but is by no means exhaustive. Two recent reviews[1,2] and one monograph[32] dealing with this subject area are comprehensive.

A series of naturally occurring sulfamoyl mononucleoside antibiotics and some synthetic analogs have been described[21-24]. In addition, analogs of DNA containing sulfides, sulfoxides and sulfones as linking groups between subunits capable of forming bonds with natural oligonucleotides have been described.[33] The β-decay of P[32] oligonucleotides is expected to give a sulfate linkate oligonucleotide; however, such sulfate linked oligonucleotides have not been reported.

Applicants have developed a novel series of compounds in which one or more of the internucleotide phosphodiester linkages in oligonucleotide analogs have been replaced by a sulfur-based linkage. This linkage is isostructural and isoelectronic with the phosphodiester. Applicants have found the linkage to be synthetically accessible, chemically robust, nuclease resistant, and capable of supporting duplex formation. In addition, such compounds would have potential as antiviral agents and utility as hybridization probes.

SUMMARY OF THE INVENTION

There is provided by this invention a compound of the formula:

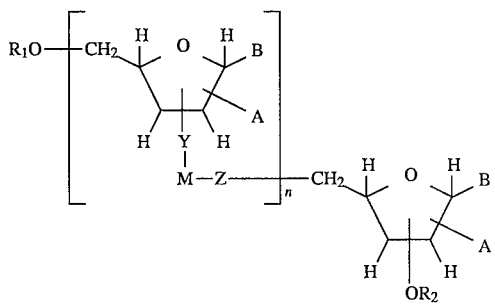

A is H, OH, $OR_8$, OQ or halogen;

B is a naturally occurring nucleic acid base or synthetic modified nucleic acid base;

Y is RN or O;

Z is $R_7N$ or O;

M is $S(=O)=O$, $P(=O)—O^-$, $P(=O)—S^-$, $P(=S)—S^-$, $P(=O)—OR_3$, $P(=O)—R_9$, $P(=O)—SR_4$ or

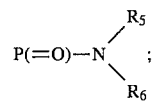

provided at least one M is $S(=O)=O$ and when M is $S(=O)=O$, only one of Y and Z are O;

n is one or greater;

R is H or alkyl;

$R_1$ is $H_2PO_3$, $H_3P_2O_5$, $H_4P_3O_7$ and their suitable salts, H or a protecting group;

$R_2$ is $H_2PO_3$, $H_3P_2O_5$, $H_4P_3O_7$ and their suitable salts, H or a protecting group;

$R_3$ is alkyl or cyanoethyl;

$R_4$ is H or alkyl;

$R_5$ is H or alkyl;

$R_6$ is H or alkyl;

$R_7$ is H or alkyl;

$R_8$ is alkyl;

$R_9$ is alkyl or cyanoethyl; and

Q is a protecting group.

In another aspect of this invention, intermediate compounds are provided:

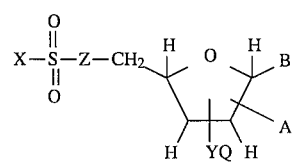

wherein:

A is H, OH, $OR_2$, OQ or halogen;

B is a naturally occurring nucleic acid base or synthetic modified nucleic acid base;

Y is RN or O;

Z is $R_1N$ or O;

X is a suitable leaving group;

Q is a protecting group;

R is H or alkyl;

$R_1$ is H or alkyl; and $R_2$ is alkyl or

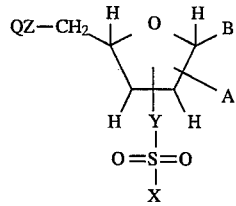

In another aspect of this invention, a hybridization probe is provided.

BRIEF DESCRIPTION OF THE DRAWINGS

FIG. 2.

DETAILED DESCRIPTION OF THE INVENTION

Figure 1:
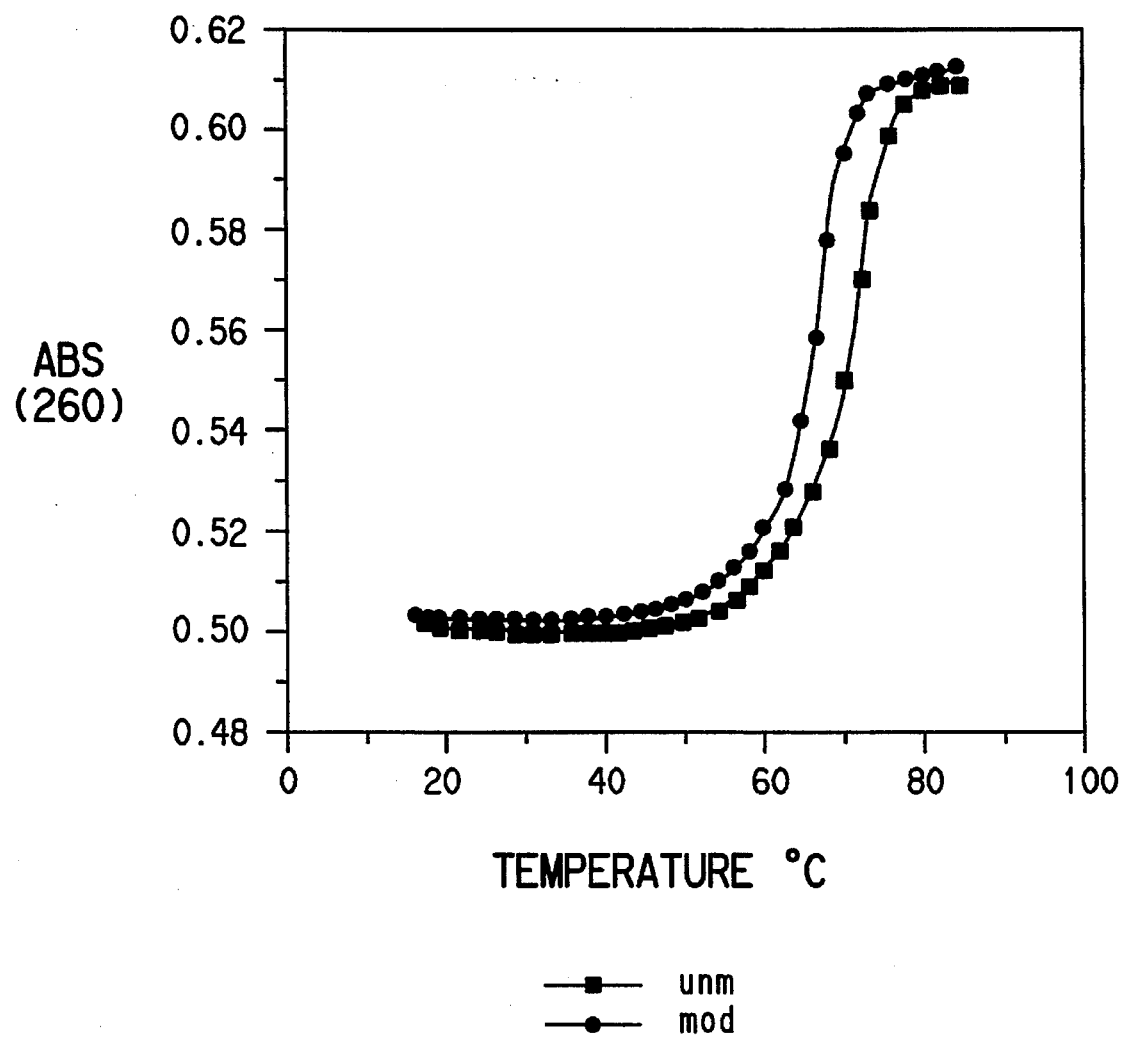
FIG. 1. Demonstrates the melting profile of the modified oligodeoxynucleotides, 9a:9c, (circles) and the two oligodeoxynucleotides containing a single sulfamate linkage in each strand, 9b:9d, (closed squares). The buffer contained 200 mM sodium at pH 7.0.

All previous attempts to replace the phosphodiester linkage in oligodeoxynucleotide analogs for the purposes of enhancing function as anti-sense reagents represent partial solutions. No single phosphodiester replacement has a completely satisfactory profile of properties. Applicants have generated a list of chemical, biochemical, and structural criteria which, if met by a compound, are likely to lead to superior functions such as anti-sense, anti-viral and triplex functions. The linkage should be: 1) isostructural (isoelectronic and isosteric) with the phosphodiester; 2) nuclease resistant; 3) uncharged at physiological pH; 4) achiral; 5) chemically stable under physiological conditions; 6) synthetically accessible; and 7) amenable to analysis.

Applicants have developed compounds with at least one novel sulfur-centered linkages which meet all of these criteria. These linkages are sulfamate esters. Conceptually these derive from the sulfate diester which is isosteric and isoelectronic with the phosphodiester. Replacement of either bridging oxygen with a nitrogen affords a sulfamate ester. Applicants have found the internucleotide sulfamate linkage to be synthetically accessible, chemically robust, nuclease resistant, and capable of supporting duplex formation.

The novel compound of this invention is represented by the formula:

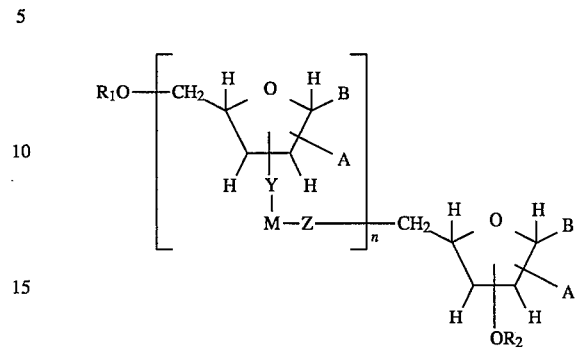

A is H, OH, $OR_8$, OQ or halogen;

B is a naturally occurring nucleic acid base or synthetic modified nucleic acid base;

Y is RN or O;

Z is $R_7N$ or O;

M is S(=O)=O, P(=O)—O⁻, P(=O)—S⁻, P(=S)—S⁻, P(=O)—$OR_3$, P(=O)—$R_9$, P(=O)—$SR_4$ or

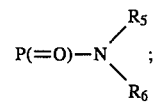

provided at least one M is S(=O)=O and when M is S(=O)=O, only one of Y and Z are O;

n is one or greater;

R is H or alkyl;

$R_1$ is $H_2PO_3$, $H_3P_2O_5$, $H_4P_3O_7$ and their suitable salts, H or a protecting group;

$R_2$ is $H_2PO_3$, $H_3P_2O_5$, $H_4P_3O_7$ and their suitable salts, H or a protecting group;

$R_3$ is alkyl or cyanoethyl;

$R_4$ is H or alkyl;

$R_5$ is H or alkyl;

$R_6$ is H or alkyl;

$R_7$ is H or alkyl;

$R_8$ is alkyl;

$R_9$ is alkyl or cyanoethyl; and

Q is a protecting group.

As far as the base (B) is concerned, no fundamental limitation is envisioned. One may include the naturally occurring nucleotide bases as well as synthetic modified nucleic acid bases such as inosine, deazaadenosine, etc. Preferably B is a residue of the naturally occurring nucleotide bases adenine, guanine, cytosine, thymine or uracil.[30, 33]

With regard to the sugar, ribonucleotides, deoxyribonucleotides, and dideoxyribonucleotides are all possible. Sugars with halogen substitution (A is halogen) and altered sugar configuration (e.g., arabinosides and alpha-ribosides) may also be contemplated.[30]

In the above compound, n is at least one, but an n of up to 200 is accessible by standard methods. A compound of n greater than 200 could be made by ligation techniques.

With regard to the internucleotide linkage (M), Applicants have demonstrated the preparation of compounds with only a single sulfur-based linkage as well as the preparation of fully replaced compounds. Compounds where at least one of the sulfur based linkages of this invention is substantially near at least one terminus of the compound, are expected to be particularly useful. Such compounds will be substantially protected from exonuclease activity. Compounds that are not fully replaced with the sulfur based linkages comprise linkages as defined by M, which are as found in DNA, RNA as well as synthetic modified nucleotides known to those skilled in the art. It is understood that materials with any degree of partial replacement of phosphorous based linkages should be accessible by the methods applicants have developed. Furthermore, compounds with mixed ribose structures (e.g., single strands containing both ribonucleotides and deoxyribonucleotides) may be prepared.

Where R substituents are alkyl, alkyls of less than 5 carbon atoms are expected to be useful.

Additionally, one may attach the chemical appendages to the compounds of this invention for the purposes of stabilizing a duplex, crosslinking, or cleaving a target sequence or for facilitating transport(vide supra).[5-9,31]

Unlike the phosphodiester linkage, the sulfamate has directionality. The linkage may be oriented in one of two ways with respect to the compound terminii. The two forms will be referred to as 3'-NSO or 5'-NSO depending on whether the nitrogen is on the 3' or 5' side of the attached sulfur.

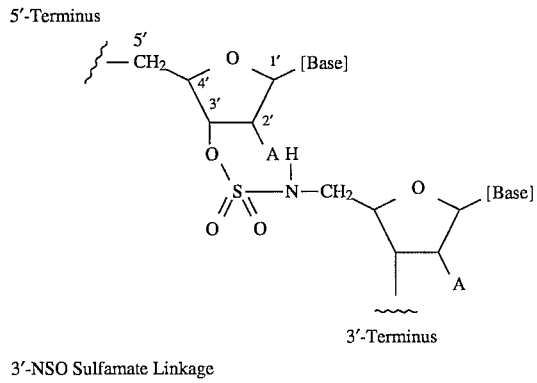

3'-NSO Sulfamate Linkage

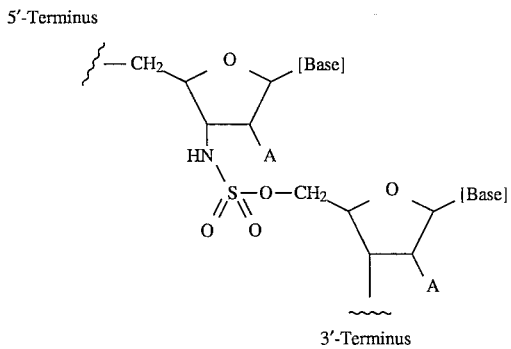

5'-NSO Sulfamate Linkage

Synthesis

Conceptually a disubstituted sulfamate can be prepared by the reaction of a hydroxy compound with a sulfamoyl-X [where X is a suitable leaving group] (Scheme 1) or by the reaction of an amino compound with alkoxysulfonyl-X (Scheme 2). Generally, the leaving group (X) is a group that is easily displaced (Examples include, halide, azide, sulfonates, etc.). Equivalent reactions with reduced sulfur reagents (e.g., sulfinyl groups) followed by oxidation may also be contemplated.

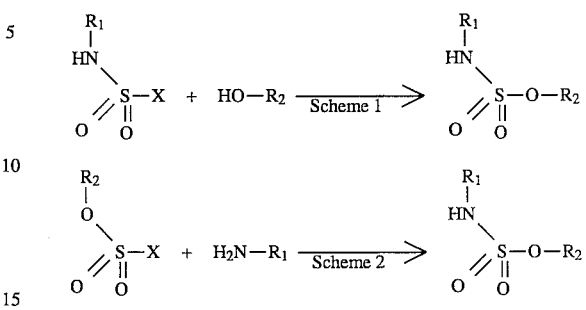

Both of these routes are feasible for the preparation of the sulfamate-linked oligonucleotide derivatives that are the subject of this application. Applicants have found one specific embodiment of Scheme 1 to be particularly efficacious. In this process, a 5'-N—(X-sulfonyl)-5'-amino-5'-deoxynucleoside intermediate is reacted with a hydroxy-bearing nucleoside or hydroxy-bearing oligonucleotide to afford a 3'-NSO sulfamate linked derivative. In this process,

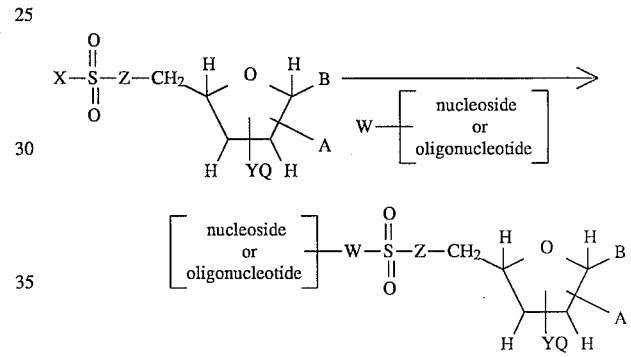

X is a suitable leaving group such as a halide, sulfonate, or azido group, with the azido group preferred. Similarly, 5'-NSO sulfamate linked derivatives may be prepared by reacting a 3'-N—(X-sulfonyl)-3'-amino-3'-deoxynucleoside with a hydroxy-bearing nucleoside or

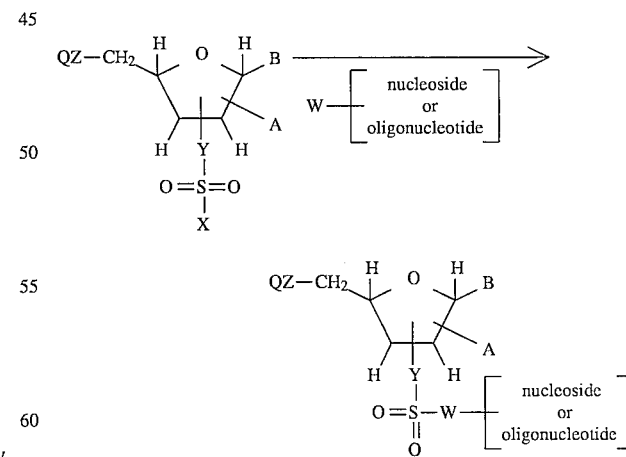

hydroxy-bearing oligonucleotide. These processes are generally carried out in the presence of a base but may also be facilitated by metal ions.

The key intermediates in these processes, the N—(X-sulfonyl)-amino-deoxynucleosides, may be conveniently prepared by the reaction of the appropriate amino-deoxynucleoside with a bifunctional sulfonating agent $X-SO_2-X'$. For example, for X=azido, the N-(azidosulfonyl)-amino-deoxynucleoside is prepared by reacting the amino-deoxynucleoside with azidosulfonyl chloride.

These N—(X-sulfonyl)-amino-deoxynucleoside intermediates may also be reacted with amino-bearing nucleosides or amino-bearing oligonucleotides, to afford sulfamide-linked oligonucleotide derivatives that are also the subject of this application.

The intermediates of this invention are compounds of the formula:

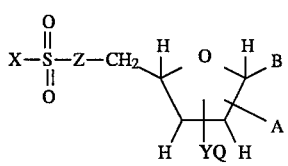

wherein:

A is H, OH, $OR_2$, OQ or halogen;

B is a naturally occurring nucleic acid base or synthetic modified nucleic acid base;

Y is RN or O;

Z is $R_1$N or O;

X is a suitable leaving group;

Q is a protecting group;

R is H or alkyl;

$R_1$ is H or alkyl; and $R_2$ is alkyl or

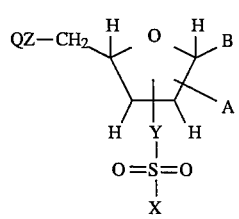

The strategy for insertion of the sulfamate linkage into larger compounds of this invention depends on the degree of substitution desired. For introduction at a single site or just a few sites, a block-dimer approach is preferred. In this approach the standard chemistry of automated oligonucleotide synthesis based the stepwise addition of single nucleotides (3' to 5' growth) via nucleoside phosphoramidites is employed.[39] At a selected point in the synthesis, a block-dimer phosphoramadite of this invention, a 5'-dimethyoxytrityl-protected, sulfamate-linked dinucleoside 3'-phosphoramidite is used in place of the normal reagent. This results in the addition of two nucleotides, linked by a sulfamate, to the 5'-terminus of the growing chain. The block multi-mer of this invention would allow n consecutive sulfamate linkages to be introduced.

The block multi-mer phosphoramidite compound of this invention is of the formula:

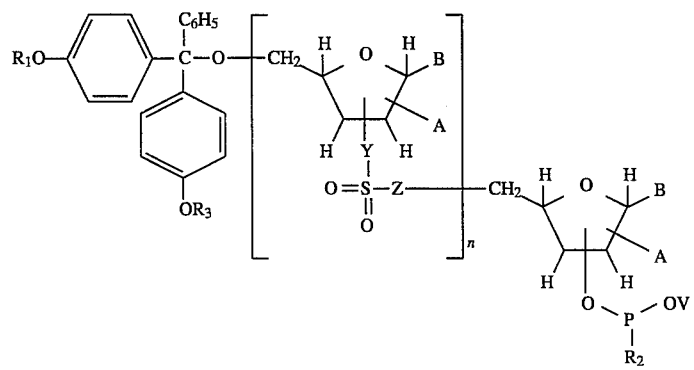

A is H, OH, $OR_4$, OQ, or halogen;

B is a naturally occurring nucleic acid base or synthetic modified nucleic acid base;

n is at least one;

$R_1$ is alkyl;

$R_2$ is dialkylamino, morpholino, piperidino or pyrrolidono;

$R_3$ is alkyl;

$R_4$ is alkyl;

Y is RN or O;

Z is RN or O;

R is H or alkyl;

Q is a protecting group; and

V is a protecting group.

R, $R_1$, $R_3$ and $R_4$ substituents with alkyls of less than 5 carbon atoms are expected to be useful.

V is a protecting group that can be cleaved under basic conditions, examples include cyanoethyl and methyl.

For all compounds of this invention, Q is alkyl or a protecting group possibly selected from acyl, trialkylsilyl, cyanoethyl, or a tetrahydropyran.

Where the A substituent contains an oxygen, three levels of protection can be imagined. In one case, the protecting group Q would be amenable to cleavage under the same conditions as for V. Another possibility is to make Q stable to the deprotection conditions used for removing V for stability reasons. The final case would be where Q is not to be removed at all, an alkyl group for example.

The issue of the stability of the sulfamate linkage is an important one in this approach. First, the linkage must be able to withstand repeated treatment under the cycling conditions: 1) removal of the 5'-trityl group with moderately strong acid; 2) coupling with a tetrazole activated phosphoramidite; and 3) oxidation with iodine under basic conditions. Applicants have found the internucleotide linkage to be fully stable to repeated treatments under these conditions. Secondly, the linkage must be able to stand up to the conditions required to cleave the nascent oligonucleotide from the resin and remove the protecting groups from the nucleotide bases. The base protection generally involves blocking the exocyclic amino groups through acylation (for C, A: benzoylation; for G: isobutyrylation). Both cleavage from the resin and base-deprotection are generally carried out by treating with concentrated aqueous ammonia. The cleavage from the resin occurs rapidly at room temperature but complete base deprotection requires more prolonged treatment at elevated temperatures. The sulfamate linkage is fully resistant to this prolonged treatment with concentrated aqueous ammonia.

Using the block dimer approach, one may synthesize compounds, oligonucleotide analogs, bearing from one to multiple sulfamate linkages. The only limitations are that the first linkage (on the 3'-terminus) may not be a sulfamate and one may not introduce consecutive sulfamates. (These limitations may be overcome, respectively, through the use of a resin linked sulfamate block dimer as a starter or through the use of block multimers.)

A different strategy is employed for the synthesis of compounds where all of the internucleotide linkages are to be replaced by the sulfamate. Here a stepwise synthesis is preferred. Synthesis is carried out in a 5'-3' direction adding a single nucleotide unit at a time. The 3'-protected-5'-azidosulfonamido monomer is activated in situ and added to the 3'-hydroxyl of the growing oligonucleotide.

This direction of chain-synthesis is the reverse of that employed in normal automated oligodeoxynucleotide synthesis. Thus the two processes are not trivially compatible. However, it is possible to conceive of cycles where either the sulfamate or the phosphodiester could be added as desired. For example, it should be possible using a 3'-azidosulfonamido-5'-protected monomer to incorporate sulfamate linkages at any point desired. This is a consequence of the extension direction now being 3' to 5', the same direction used in phosphoramidite extension.

In general an activated monomer approach is superior to a block dimer approach in that: a) all possible sequences can be addressed; and b) only four, as opposed to sixteen reagents are required.

The sulfamate-linked oligonucleotides may be useful as hybridization probes and as structural analogs for the study of protein/nucleic acid interactions.

Duplex Formation:

To function as an anti-sense reagent, the compound of this invention must retain the ability to recognize (hybridize to, anneal to, form duplex with) a complementary sequence. For short oligonucleotides, this may be conveniently assayed by observing the changes in UV absorption which accompany duplex formation. Generally, the absorption at 260 nm is measured as a function of temperature.

To study the effect of replacing a single phosphodiester linkage with the sulfamate on duplex formation, a pair of modified complementary 18-mers, each having a single sulfamate linkage, were compared to the corresponding pair of unmodified 18-mers. The two pairs showed virtually identical melting profiles (smooth S-curves) with the curve for the modified pair displaced to a slightly lower temperature. That the magnitude of the absorption change is identical and the curves are nearly identical in shape suggest that the duplex is perturbed very little by the sulfamate linkage and that it undergoes single-domain melting. The slightly lower transition temperature indicates that the modified duplex is slightly less stable than its unmodified counterpart under these conditions.

Attempts to demonstrate annealing of a T-homopolymer bearing all sulfamate linkages to a short dA homopolymer (with phosphodiesters) have been unsuccessful. This is somewhat perplexing but a similar phenomenon has been observed with carbamates and methylphosphonates: oligoTs (and Us) anneal poorly or not at all to polyA, yet sequences with other bases anneal well[17,20]. This may be a peculiarity of oligoTs when the linkage is uncharged.

The annealing of a sulfamate-linked adenosine dimer to polyU has been demonstrated. Here the interaction was very strong with a transition temperature some 10 degrees higher than the corresponding unmodified adenosine dimer.

Nuclease Resistance:

For stability in vivo, it is desirable that an anti-sense reagent be resistant to exonucleases, which digest from either terminus in a stepwise fashion, and endonucleases, which cleave in the middle of the chain.

To test for exonuclease resistance, several compounds of this invention having a single sulfamate linkage were subjected to prolonged treatment with a mixture of an exonuclease, snake venom phosphodiesterase, and alkaline phosphatase (to facilitate analysis). In each case, the sulfamate link was recovered intact (as the dimer) with the rest of the compounds fully digested to its constituent nucleosides.

Endonuclease resistance was tested by examining the cleavage of a short double stranded oligomer containing the Nsi 1 restriction endonuclease recognition sequence. This endonuclease normally cuts both strands within its recognition sequence in a staggered fashion. Replacement of the phosphodiester bond at the cleavage site in either or both strands conferred resistance to cleavage in the altered strand(s).

EXAMPLES

Example 1

Preparation of
$N_6$-benzoyl-3'-O-t-butyldimethylsilyl-5'-sulfamoylazido-2',5'-dideoxyadenosine A mixture of 8.9 g (24 mmol) of 5'-Azido-N6-benzoyl-2',5'-dideoxyadenosine (which can be prepared as in reference 36), 5.4 g (35 mmol) of t-butyldimethylsilyl chloride, and 3.3 g (48 mmol) of imidazole in 100 ml of anhydrous dimethylformamide (DMF) was stirred at room temperature (RT) for 20 hr. The solvent was removed under vacuum, and the residue was partitioned between one half saturated brine and EtOAc (2×200 ml). The combined organic layers were washed with brine, dried with sodium sulfate (dried), and evaporated (evap.). Purification by chromatography on silica (silica gel (240–400 mesh) from EM Science) using 20 to 40% EtOAc/DCM gave 11.1 g of 5'-Azido-N6-benzoyl-3'-O-t-butyldimethylsilyl-2',5'-dideoxyadenosine as a white foam: NMR (300 MHz,d6-DMSO) δ11.25 (br, 1H), 8.78 (s,1H), 8.71 (s, 1H), 8.05 (m, 2H), 7.5–7.7 (m, 3H), 6.52 (t, 1H,J=7 Hz), 4.72 (m, 1H), 4.02 (m,1H), 3.67 (dd,1H, J=13,7

Hz), 3.56 (dd,1H,J=13,5 Hz), 3.09 (m, 1H), 2.43 (m,1H), 0.92 (s,9H), 0.14 (s,6H).

A mixture of 5.08 g (10.4 mmol) of 5'-Azido-N6-benzoyl-3'-O-t-butyldimethylsilyl-2',5'-dideoxyadenosine and 2.1 g of 10% Pd/C in 69 ml of ethanol and 3.0 ml of acetic acid was stirred under 1 atm. of hydrogen for 4 hr. The slurry was filtered through celite washing with methanol p-Toluenesulfonic acid monohydrate (1.97 g, 10.4 mmol) was added and the mixture was agitated until dissolution. The solution was evap., and the resulting solid was chromatographed on silica (1 to 12% methanol/DCM) giving 4.63 g of 5'-Amino-N6-benzoyl-3'-O-t-butyldimethylsilyl-2',5'-dideoxyadenosine, p-toluenesulfonate salt: NMR (300 MHz, d6-DMSO) δ8.76 (s,1H), 8.74 (s,1H), 8.05 (d,2H, J=8 Hz ), 7.67 (t,1H,J=8 Hz), 7.57 (t,2H,J=8 Hz), 7.48 (d,2H,J=8 Hz), 7.11 (d,2H,J=8 Hz), 6.53 (t,1H,J=7 Hz), 4.68 (m,1H), 4.01 (m,1H), 3.06 (m,2H), 2.56 (m,1H), 2.39 (m,1H), 2.29 (s,3H), 0.93 (s,9H), 0.15 (s,6H).

A mixture of 4.24 g (6.68 mmol) of 5'-amino-N6-benzoyl-3'-O-t-butyldimethylsilyl-2',5'-dideoxyadenosine and 4 Å molecular sieves (~5 g) in 10 ml of anhydrous acetonitrile and 20 ml of anhydrous DCM was stirred under nitrogen for 2 hr. After adding 0.93 ml (6.68 mmol) of triethylamine, the mixture was stirred for 5 min, and 0.42 ml of chlorosulfonylazide (1M in acetonitrile) were added. After stirring the reaction for 1 hr., the slurry was filtered and the filtrate was partitioned between water and EtOAc (2×100 ml). The combined organic layers were washed with brine, dried, and evap. Purification using chromatography on silica (1 to 3% MeOH/DCM) gave 0.89 g of N6-benzoyl-3'-O-t-butyldimethylsilyl-5'-sulfamoylazido-2',5'-dideoxyadenosine as a white foam: NMR (300 MHz,d6-DMSO) δ11.22 (br,1H), 9.28 (br,1H), 8.75 (s,1H), 8.71 (s,1H), 8.05 (d,2H, J=8 Hz), 7.66 (t,1H,J=8 Hz), 7.56 (t,2H,J=8 Hz), 6.52 (t,1H,J=8 Hz), 4.67 (m,1H), 4.00 (m,1H), 3.07 (m,1H), 2.34 (m,1H), 0.93 (s,9H), 0.15 (s,6H). IR (KBr) 3400, 3080 2950, 2930, 2880, 2860, 2130, 1700, 1610, 1585, 1510, 1370, 1170 cm−1.

Example 2

Preparation of N6-benzoyl-3'-O--t-butyldimethylsilyl-5'-sulfamoylazido-2',5'-dideoxycytidine A mixture of 12.09 g (35.1 retool) of 5'-Azido-N6-benzoyl-2',5'-dideoxycytidine (which can be prepared as in reference 36), 7.94 g (52.7 mmol) of t-butyldimethylsilyl chloride, and 4.78 g (70.3 mmol) of imidazole were stirred in 70 ml of anhydrous DMF under nitrogen at RT for 20 hr. The DMF was removed under vacuum, and the resulting mixture was dissolved in DCM and loaded directly on a column of silica. A 25% EtOAc/DCM solution was used to elute the product from the column. Evap. of the fractions containing the product gave 13.35 g of 5'-Azido-N6-benzoyl-3'-O-t-butyldimethylsilyl-2',5'-dideoxycytidine as a white foam: NMR (300 MHz,d6-DMSO) δ11.31 (br,1H), 8.18 (d,1H,J=8 Hz), 8.01 (m,2H), 7.63 (m,1H), 7.56 (t,2H, J=7 Hz), 7.39 (d,1H,J=8 Hz), 6.20 (t,1H,J=7 Hz), 4.38 (m,1H), 3.96 (m,1H), 3.68 (dd,1H,J=13,6 Hz), 3.61 (dd,1H, J=13,5 Hz), 2.30 (m,1H), 0.88 (s,9H), 0.10 (s,6H).

A mixture of 6.88 g (15 mmol) of 5'-Azido-N6-benzoyl-3'-O-t-butyldimethylsilyl-2',5'-dideoxycytidine and 3.0 g of 10% Pd/C in 130 ml of ethanol and 5 ml of acetic acid was stirred under 1 atm. of hydrogen for 4 hr. The slurry was filtered through celite washing with methanol. p-Toluenesulfonic acid monohydrate (2.85 g, 15 mmol) was added and the mixture was agitated until dissolution. The solution was evap., and the resulting solid was chromatographed on silica (1 to 12% methanol/DCM) giving 6.32 g of pure 5'-amino-N6-benzoyl-3'-O-t-butyldimethylsilyl-2',5'-dideoxycytidine p-toluenesulfonate salt as a tan solid: NMR (300 MHz,d6-DMSO) δ8.31 (d,1H,J=8 Hz), 8.02 (d,2H,J=8 Hz), 7.64 (m,1H), 7.52 (m,4H), 7.38 (d,1H,J=8 Hz), 7.12 (d,2H,J=8 Hz), 6.19 (t,1H,J=6.5 Hz), 4.43 (m,1H), 3.97 (m,1H), 3.02 (m,2H), 2.30 (m,5H), 0.89 (s,9H), 0.11 (s,6H).

A mixture of 3.40 g (5.63 mmol) of 5'-amino-N6-benzoyl-3'-O-t-butyldimethylsilyl-2',5'-dideoxycytidine p-toluenesulfonate salt and 4 Å molecular sieves (~5 g) in 30 ml of 50% anhydrous DCM/acetonitrile was stirred under nitrogen for 1 hr After cooling to 0° C., 0.78 ml (5.63 mmol) of triethylamine was added and stirring was continued for 10 min. Finally 3.9 ml (3.9 mmol) of chlorosulfonylazide (1M in acetonitrile) was added, the cold bath was removed, and the reaction was stirred for 2.5 hr. The slurry was filtered, and the filtrate was partitioned between one half saturated brine and 300 ml of EtOAc. The organic layer was washed with brine, dried, and evap. Purification by chromatography on silica (1 to 4% methanol/DCM) gave 0.99 g of product that contained two impurities. Furthur chromatography afforded pure N6-benzoyl-3'-O-t-butyldimethylsilyl-5'-sulfamoylazido-2',5'-dideoxycytidine as a white foam: NMR (300 MHz,d6-DMSO) δ11.27 (br,1H), 9.30 (br,1H), 8.21 (d,1H,J=8 Hz), 8.01 (m,2H), 7.62 (m,1H), 7.50 (t,2H,J=8 Hz), 7.37 (d,1H,J=8 Hz), 6.17 (t,1H,J=6.5 Hz), 4.39 (m,1H), 3.95 (m,1H), 3.35 (m,2H), 2.27 (m,2H), 0.89 (s,9H), 0.10 (s,6H).

Example 3

Preparation of 3'-O-t-butyldimethylsilyl-N4-i-butyryl-O6- (4-nitrophenethyl)-5'--sulfamoylazido-2',5'-dideoxyguanosine Using the procedure in reference 37, 5.00 g (17.5 mmol) of 2'-deoxyguanosine (Sigma, St. Louis, Mo.), 63 ml of anhydrous DCM, 13 ml of anhydrous pyridine, and 9.3 ml (88 mmol) of isobutyryl chloride gave 10.34 g of crude N4, (3',5'-O-)-tri-i-butyryl-2'-deoxyguanosine.

After dissolving 10.34 g (~17 mmol) of crude N4, (3',5'-O-)-tri-i-butyryl-2'-deoxyguanosine in 70 ml of anhydrous DCM under nitrogen, 8.91 g (34 mmol) of triphenylphosphine and 5.68 g (34 mmol) of 4-nitrophenethyl alcohol were added and dissolved with stirring After cooling to 0° C., 5.3 ml (34 mmol) of diethyldiazodicarboxylate were added over 5 minutes (min). The cold bath was removed, and the reaction was stirred for 18 hr. A TLC of the reaction mixture (10% methanol/DCM) indicated some of the starting material was still present. Triphenylphosphine (4.45 g), 4-nitrophenethyl alcohol (5.30 g), and diethyldiazodicarboxylate (2.65 ml) were added sequentially, and the mixture was stirred another one hr. The solvent was evaporated, and the residue was used directly in the next reaction. A sample was purified by chromatography on silica (1 to 5% methanol/DCM) to give N4, (3',5'-O-tri-i-butyryl-O6-(4-nitrophenethyl)-2'-deoxyguanosine as a white foam: NMR (300 MHz, CdCl3) δ8.17 (d,2H,J=8 Hz), 8.07 (br, 1H), 7.97 (s, 1H), 7.53 (d, 2H, J=8Hz), 6.36 (dd, 1H, J=7,6 Hz), 5.43 (m, 1H), 4.84 (t,2H, J=7 Hz), 4.54 (dd, 1H, j=12,5 Hz), 4.39 (m, 2H), 3.33 (t,2H, J=7 Hz), 2.5–3.1 (m,5H), 1.39 (d,6H,J=7 Hz), 1.32 (d,6H,J=7 Hz), 1.26 (d,3H,J=7 Hz), 1.24 (d,3H, J=7 Hz);

Crude N4, (3',5=-O-) -tri-i-butyryl-O6-(4-nitrophenethyl)-2'-deoxyguanosine (~17 mmol) was dissolved in 400 ml of methanol and 400 ml of 27% ammonium hydroxide were added. The mixture was cloudy so enough methanol was added (100 ml) to make the reaction homogeneous. After stirring for 20 hr at RT, the solvents were evap. and the residue was taken up in 100 ml of DCM. Enough hexane was added to make the solution cloudy. After standing overnight, the light yellow crystals were collected to give 5.83 g of N4-i-butyryl-O6-(4-nitrophenethyl)-2'-deoxyguanosine. A second crystallization gave an additional material for a total of 8 .60 g of N4-i-butyryl-O6-(4-nitrophenethyl)-2'-deoxyguanosine: NMR (300 MHz, 20% d4-methanol/CDCl3) δ8.18 (d,2H,J=9 Hz), 8.17 (s,1H), 7.57 (d,2H,J=9 Hz), 6.38 (t,1H,J=7 Hz), 4.84 (t,2H,J=7 Hz), 4.72 (m,1H), 4.07 (q,1H, J=4 Hz), 3.83 (ddd,2H,J=33,12,4 Hz), 3.33 (t,2H,J=7 Hz), 2.75–2.9 (m,2H), 2.44 (ddd,1H,J=14,7,4 Hz), 1.37 (d,6H, J=8 Hz).

A solution of 7.28 g (14.9 mmol) of N4-i-butyryl-O6-(4-nitrophenethyl)-2'-deoxyguanosine in 75 ml of anhydrous pyridine was cooled to 0° C. under nitrogen. After adding 2.84 g (14.9 mmol) of p-toluenesulfonyl chloride, the reaction was stirred at 0° C. for 2 hr and then at 5° C. for 18 hr. The pyridine was evap., and the residue was partitioned between water and EtOAc. The organic layer was washed with brine, dried, and evap. to give 6.22 g. Purification by chromatography on silica (1 to 5% methanol/DCM) gave 4.08 g of N4-i-butyryl-O6-(4-nitrophenethyl)-5'-O-p-toluenesulfonyl-2'-deoxyguanosine as a white foam: (300 MHz, 20% d6-DMSO) δ10.34 (br,1H), 8.24 (s,1H), 8.19 (d,2H,J=8 Hz), 7.67 (d,2H,J=8 Hz), 7.61 (d,2H,J=8 Hz), 7.22 (d,2H, J=8 Hz), 6.38 (t,1H,J=7 Hz), 5.46 (d,1H,J=5 Hz), 4.82 (t,2H,J=7 Hz), 4.64 (m,1H), 4.33 (ddd,2H, J=26,12,8 Hz), 3.97 (m,1H), 3.35 (t,2H,J=7 Hz), 2.82 (m,2H), 2.27 (s,3H)i, 1.12 (d,3H,J=7 Hz), 1.10 (d,3H,J=7 Hz).

A solution of 4.08 g (6.35 mmol) of N4-i-butyryl-O6-(4-nitrophenethyl)-5'-O-p-toluenesulfonyl-2'-deoxyguanosine and 467 mg (9.52 mmol) of lithium azide (Kodak, Rochester, N.Y.) in 21 ml of anhydrous DMF was heated to 100° C. for 3 hr. The solvent was removed under vacuum. The residue was partitioned between water and EtOAc. The organic layer was washed with brine, dried, and evap. to give 3.95 g of crude product. Purification by chromatography on silica (1 to 10% methanol/DCM) gave 1.47 g of the less polar material and 419 mg of the more polar material. The less polar material was a white foam and was found to be 5'-azido-N4-i-butyryl-O6-(4-nitrophenethyl)-2',5'-dideoxyguanosine: NMR (300 MHz, d6-DMSO) δ10.40 (br,1H), 8.41 (s,1H), 8.18 (d,2H,J=8 Hz), 7.64 (d,2H,J=8 Hz), 6.37 (t,1H,J=7 Hz), 5.46 (d,1H,J=4 Hz), 4.79 (t,2H,J=7 Hz), 4.63 (m,1H), 3.97 (m,1H), 3.86 (dd,1H,J=13,8 Hz), 3.53 (dd,1H, J=13.5 Hz), 3.36 (t,2H,J=7 Hz), 3.05(m,1H), 2.84 (m,1H), 2.28 (ddd,1H,J=14,6,3 Hz), 1.12 (d,6H,J=8 Hz).

In the same manner as for 5'-Azido-N6-benzoyl-3'-O-t-butyldimethylsilyl-2',5'-dideoxycytidine, 1 47 g (2 87 mmol) of 5'-azido-N4-i-butyryl-O6- (4-nitrophenethyl)-2',5'-dideoxyguanosine, 0 65 g (4.3 mmol) of t-butyldimethylsilyl chloride, 0.39 g (5.7 mmol) of imidazole, and 10 ml of anhydrous DMF was used to obtain after chromatography on silica (10% EtOAc/DCM) 1.49 g of 5'-azido-3'-O-t-butyldimethylsilyl-N4-i-butyryl-O6-(4-nitrophenethyl)-2'-dideoxyguanosine as a white foam: NMR (300 MHz, d6-DMSO) δ10.40 (br,1H), 8.40 (s,1H), 8.18 (d,2H,J=9 Hz), 7.65 (d,2H,J=9 Hz), 6.35 (t,1H,J=7 Hz), 4.78 (t,2H,J=7 Hz), 4.73 (m,1H), 3.94 (m,1H), 3.84 (dd,1H,J=13,8 Hz), 3.56 (dd,1H,J=13,5 Hz), 3.31 (t,2H,J=7 Hz), 3.10 (m,1H), 2.82 (m,1H), 2.29 (m,1H), 1.10 (d,6H,J=7 Hz), 0.89 (s,9H), 0.14 (s,3H), 0.12 (s,3H).

A mixture of 100 mg (0.159 mmol) of 5'-azido-3'-O-t-butyldimethylsilyl-N4-i-butyryl-O6-(4-nitrophenethyl)-2', 5'-dideoxyguanosine, 0.064 ml (0.64 mmol) of 1,3-propanedithiol, 0.089 ml (0.64 mmol) of triethylamine, and 1 ml of methanol was stirred under nitrogen at RT for 4 days. After adding 0.5 ml of acetic acid, the reaction was concentrated under vacuum. Purification by chromatography on silica (1 to 15% methanol/DCM) gave 121 mg of the acetic acid salt of the product. This material was partitioned between saturated potassium carbonate and EtOAc. The organic layer was dried and evap to give 91 mg of 5'-amino-3'-O-t-butyldimethylsilyl-N4-i-butyryl-O6-(4-nitrophenethyl)-2',5'-dideoxyguanosine: NMR (300 MHz, CDCl3) δ8.17 (d,2H,J=8 Hz), 7.98 (s,1H), 7.90 (br,1H), 7.52 (d,2H, J=8 Hz), 6.28 (t,1H,J=7 Hz), 4.80 (t,2H,J=7 Hz), 4.71 (m,1H), 3.93 (q,1H,J=4 Hz), 3.32 (t,2H,J=7 Hz), 3.04 (dd, 1H,J=14,4 Hz), 2.93 (dd,1H,J=14,6 Hz), 2.84 (m,1H), 2.39 (m,1H), 1.28 (d,6H,J=7 Hz), 0.93 (s,9H), 0.13 (s,3H), 0.11 (s,3H).

A solution of 90 mg (0.15 mmol) of 5'-amino-3'-O-t-butyldimethylsilyl-N4-i-butyryl-O6-(4-nitrophenethyl)-2', 5'-dideoxyguanosine in 2 ml of anhydrous DCM was stirred at RT under nitrogen while 0.11 ml of chlorosulfonylazide (1M in acetonitrile) was added. After stirring for 1 hr., the solution was partitioned between one half saturated brine and EtOAc. The organic layer was washed with brine, dried, and evap. The residue was purified by chromatography on silica (1 to 3% methanol/DCM) to give 18 mg of 3'-O-t-butyldimethylsilyl-N4-i-butyryl-O6-(4-nitrophenethyl)-5'-sulfamoylazido-2',5'-dideoxyguanosine: NMR (300 MHz, CDCl3) δ8.67 (br,1H), 8.46 (t,1H,J=6 Hz), 8.16 (d,2H,J=8 Hz), 7.81 (s,1H), 7.54 (d,2H,J=8 Hz), 6.17 (dd,1H,J=8,6 Hz), 4.87 (m,3H), 4.17 (m,1H), 3.57 (m,1H), 3.34 (t,2H,J=7 Hz), 2.98 (m,1H), 2.65 (m,1H), 2.25 (m,1H), 1.27 (d,3H,J=7 Hz), 1.26 (d,3H,J=7 Hz), 0.93 (s,9H), 0.16 (s,3H), 0.14 (s,3H).

Example 4

Preparation of 3'-O-t-butyldimethylsilyl-5'-sulfamoylazido-5'-deoxythymidine

A solution of 25.0 g (93.6 mmol) of 5'-azido-5'-deoxythymidine (which can be prepared as in reference 36), 21.1 g (140 mmol) of t-butyldimethylsilyl chloride, and 12.7 g (187 mmol) imidazole in 190 ml of anhydrous DMF was stirred at RT under nitrogen for 18 hr. The DMF was removed under vacuum. The oil was partitioned between ether (500 ml) and 1N NaOH (2×300 ml). The aqueous layers were cooled with ice, and 650 ml of 1N HCl were added. The product was extracted with EtOAc (2×750 ml), and the organic layer was washed with brine, dried, and evap. After remaining under high vacuum for 24 hr, the oil crystallized to give 27.9 g of 5'-azido-3'-O-t-butyldimethylsilyl-5'-deoxythymidine as a white solid: NMR (300 MHz,d6-DMSO) δ11.34 (br,1H), 7.50 (s,1H), 6.16 (t,1H,J=7 Hz), 4.36 (m,1H), 3.84 (m,1H), 3.55 (m,2H), 2.34 (m,1H), 2.05 (m,1H), 1.79 (s,3H), 0.86 (s,9H), 0.08 (s,6H).

A mixture of 15.0 g (39.3 mmol) of 5'-azido-3'-O-t-butyldimethylsilyl-5'-deoxythymidine and 4.0 g of 10% Pd/C in 200 ml of EtOAc was stirred vigorously under 1 atm. of hydrogen for 4.5 hr. The slurry was filtered through celite, rinsing with methanol. The filtrate was evap. to give 15.5 g of a thick oil (contains some solvent). A sample was purified by chromatography on silica (2–10% methanol/DCM) to give pure 5'-amino-3'-O-t-butyldimethylsilyl-5=-deoxythymidine as a white solid: NMR (300 MHz, d6-DMSO) δ7.64 (s,1H), 6.13 (dd,1H,J=8,6 Hz), 4.37

(m,1H), 3.65 (m,1H), 2.78 (m,2H), 2.21 (m,1H), 2.01 (ddd, 1H,J=12,6,4 Hz), 1.79 (s,3H), 0.88 (s,9H), 0.08 (s,6).

A mixture of 5.52 g of 5'-amino-3'-O-t-butyldimethylsilyl-5'-deoxythymidine and 168 mg of ammonium sulfate in 150 ml of hexamethyldixilazane (HMDS) was heated to dissolution under nitrogen. After stirring at RT for 18 hr, the slurry was heated to 80° C. for 2 hr. The HMDS was removed under vacuum to give a thick oil which was dissolved in 45 ml of anhydrous acetonitrile under nitrogen. This solution was added to an addition funnel and dripped into 10 ml of chlorosulfonylazide (1M in acetonitrile) precooled to 0° C. over 25 minutes. After the addition, the cold bath was removed, and the mixture was stirred for 1 hr. The reaction was poured onto 200 ml of half saturated brine and extracted with EtOAc (2×200 ml). The combined organic layers were washed with brine, dried, and evap. to give 5.29 g of a solid. Purification by chromatography on silica (1 to 5% methanol/DCM) gave 3.70 g of reasonably pure 3'-O-t-butyldimethylsilyl-5'-sulfamoylazido-5'-deoxythymidine as a tan foam: NMR (300 MHz,CDCl3) δ8.57 (br,1H), 7.02 (s,1H), 6.88 (br,1H), 5.75 (t,1H,J=8 Hz), 4.49 (m,1H), 4.04 (m,1H), 3.48 (m,2H), 2.72 (m,1H), 2.18 (m,1H), 1.92 (s,3H), 0.89 (s,9H), 0.11 (m,6H).

Example 5

Preparation of 3'-O-acetyl-5'-sulfamoylazido-5'-deoxythymidine

A mixture of 1.00 g (3.53 mmol) of 5'-amino-3'-O-acetyl-5'-deoxythymidine (which can be prepared as in reference 38) and 94 mg of ammonium sulfate was stirred in 20 ml of HMDS under nitrogen at RT for 18 hr. The slurry was gently heated (60° C.) for 24 hr. The HMDS was removed under vacuum into a trap at −78° C. Acetonitrile (40 ml) was added under nitrogen giving a homogenous solution. After adding 5.0 ml of chlorosulfonylazide (1.0M in acetonitrile) to the reaction, the mixture was stirred for 1.5 hr. Water (50 ml) was added and the product was extracted with EtOAc (2×150 ml). The organic layers were washed with brine, dried, and evap. giving 0.89 g of a solid. Purification by chromatography on silica (1 to 5% methanol/DCM) gave 0.64 g of pure 3'-O-acetyl-5'-sulfamoylazido-5'-deoxythymidine as a foam: NMR (300 MHz, d6-DMSO) δ11.40 (Br,1H), 9.31 (Br,1H), 7.59 (s,1H), 6.17 (dd,1H,J=7.5,6.5 Hz), 5.14 (m,1H), 4.03 (m,1H), 3.44 (m,2H), 2.47 (m,1H), 2.25 (m,1H), 2.07 (s,3H), 1.80 (s,3H); IR (film) 3200, 2920, 2840, 2135, 1730, 1685, 1365, 1240, 1170 cm−1; Mass Spectrum (FAB) meas 388.98 m/z, calcd for C12H16N6O7S 389.08 (M+H);

Example 6

Preparation of 5'-dimethoxytrityl-3'-sulfamoylazido-3'-deoxythymidine

A slurry of 2.17 g of 3'-azido-3'-deoxythymidine (Aldrich, Milwaukee, Wis.) and 0.91 g of 10% Pd/C in 25 ml of ethanol were vigorously stirred under 1 atm. of hydrogen for 4 hr. The mixture was filtered through celite, washed with methanol, and the filtrate was evap. Purification by chromatography on silica (2 to 40% methanol/DCM) gave 1.72 g of 3'-amino-3'-deoxythymidine as a light yellow solid: NMR (300 MHz,d6-DMSO) δ7.76 (s,1H), 6.07 (t,1H,J=6 Hz), 4.97 (m,1H), 3.5–3.7 (m,3H), 3.39 (q,1H,J=7 Hz), 3.33 (br,2H), 1.9–2.15 (m,2H), 1.77 (s,3H).

A solution of 1.04 g of 3'-amino-3'-deoxythymidine, 0.90 ml of triethylamine, and 1.5 ml of ethyl trifluoroacetate in 10 ml of methanol was stirred under nitrogen at RT for 20 hr. Evaporation gave a product that was used without purification. A sample was subjected to column chromatography on silica (1 to 20% methanol/DCM) affording pure 3'-trifluoroaceamido-3'-deoxythymidine: NMR (300 MHz,d6-DMSO) δ11.33 (br,1H), 9.84 (br,1H), 7.76 (s,1H), 6.26 (t,1H,J=7 Hz), 5.15 (t,1H,J=5 Hz), 4.47 (m,1H), 3.89 (m,1H), 3.6 (m,2H), 2.27 (m,2H), 1.78 (s,3H).

To a solution of crude 3'-trifluoroaceamido-3'-deoxythymidine, in pyridine was added 1.2 ml of triethylamine, 0.10 g of N,N-dimethylaminopyridine, and 2.2 g of dimethoxytrityl chloride under nitrogen. After stirring for 18 hr., the solvent was evap. The dark oil was partitioned between one half saturated bicarbonate and EtOAc. The organic layer was washed with brine, dried, and evap. Purification by chromatography on silica (1 to 7% methanol/DCM) gave 2.18 g of pure 5'-dimethoxy-trityl-3'-trifluoroacetamido-3'-deoxythymidine as a yellow solid: NMR (300 MHz, CDCl3) δ8.89 (br,1H), 8.31 (d,1H,J=7 Hz), 7.65 (s,1H), 7.2–7.45 (m,9H), 6.84 (d,4H,J=9 Hz), 6.51 (t,1H,J=7 Hz), 4.72 (m,1H), 4.09 (m,1H), 3.78 (s,6H), 3.53 (m,2H), 2.45 (m,2H), 1.64 (s,3H).

A solution of 1.54 g of 5'-dimethoxytrityl-3'-trifluoroacetamido-3'-deoxythymidine in methanol was saturated with ammonia gas at RT. The reaction vessel was sealed for 4 days. After the solvent was evap., the residue was purified using chromatography on silica (1 to 10% methanol/DCM) giving 1.17 g of 3'-amino-5'-O-dimethoxytrityl-3'-deoxythymidine: NMR (300 MHz,d6-DMSO) δ7.51 (s,1H), 7.2–7.45 (m,9H), 6.88 (d,4H,J=8 Hz), 6.14 (t,1H,J=6 Hz), 3.74 (s,6H), 3.68 (m,1H), 3.50 (q,1H,J=7 Hz), 3.33 (br,2H), 3.21 (m,2H), 2.21 (m,1H), 2.03 (m,1H), 1.47 (s,3H).

In the same manner as with example 4, 605 mg of 3'-amino-5-O-dimethoxytrityl-3'-deoxythymidine, 20 ml of HMDS, 0.78 ml of chlorosulfonylazide (1M in acetonitrile), nitrile), and 6 ml of anhydrous acetonitrile were used to obtain (after purification on silica using 1 to 5% methanol/DCM) 217 mg of 5'-dimethoxytrityl-3'-sulfamoylazido-3'-deoxythymidine as a light orange solid: NMR (300 MHz, CDCl3) δ7.58 (s,1H), 7.2–7.4 (m,9H), 6.85 (d,4H,J=9 Hz), 6.55 (t,1H,J=7 Hz), 4.31 (m,1H), 4.23 (m,1H), 3.78 (s,6H), 3.50 (dd,1H,J=11,3 Hz), 3.39 (dd,1H,J=11,3 Hz), 2.46 (m,2H), 1.47 (s,3H).

Example 7

Preparation of the sulfamate linked dimer d(AST)

Stirred a mixture of 480 mg of the compound from Example 4 and 493 mg of N6-benzoyl-5'-dimethoxytrityl-2'-deoxyadenosine (Aldrich, Milwaukee, Wis.) in 7 ml of dry acetonitrile with some 4 Å mol. sieves for 2 hr. Added 0.17 ml of triethylamine to the reaction and stirred 18 hr. The mixture was filtered and evap. Purification by chromatography on silica (1–7% methanol/DCM) gave 621 mg of (DMTO)A$^{Bz}$sT(OTBDMS) as a white solid: NMR (300 MHz, d6-DMSO) δ11.33 (s,1H), 11.23 (br,1H), 8.58 (s,1H), 8.57 (s,1H), 8.51 (br,1H), 8.05 (m,2H), 7.5–7.7 (m,4H), 7.34 (m,2H), 7.21 (m,7H), 6.80 (dd,4H,J=8,5 Hz), 6.52 (t,1H,J=7 Hz), 6.14 (t,1H,J=7 Hz), 5.28 (m,1H), 4.37 (m,2H), 3.81 (m,1H), 3.71 (s,6H), 3.29 (m,4H), 3.14 (dd,1H,J=17,5 Hz), 2.78 (m,1H), 2.26 (m,1H), 2.04 (m,1H), 1.77 (s,3H), 0.87 (s,9H), 0.09 (s,6H). mass spectrum (FAB) m/z 1075.47 (assigned M+H), calcd for C54H62N8O12SSi+H 1075.40. IR (CH2C12) 3380, 3180, 3060, 2960, 2930, 2860, 1695, 1610, 1585, 1510, 1360, 1180, 1250 CM–1.

The fully protected dimer, (DMTO) $A^{Bz}$sT(OTBDMS), was treated with a total of 6 ml of 1M tetra-n-butylammonium fluoride/THF (Aldrich) in four equal aliquots in one hr. intervals (small s designates sulfamate linkage). After the final additon, the reaction was stirred for 1 hr. The solution was partioned between 1M sodium dihydrogen phosphate and ethyl acetate (EtOAc). The organic layer was washed with brine, dried, and evap. The crude product was chrom. on silica (1–7% methanol/DCM) gaving 420 mg of (DMTO)$A^{Bz}$sT(OH) as a solid: NMR (300 MHz,d6-DMSO)×11.31 (Br,1H), 11.22 (br,1H), 8.58 (s,2H), 8.47 (br,1H), 8.03 (m,2H), 7.45–7.7 (m,4H), 7.34 (m,2H), 7.20 (m,7H), 6.81 (dd,4H,J=8,5 Hz), 6.52 (t,1H,J=7 Hz), 6.14 (t,1H,J=7 Hz), 5.39 (d,1H,J=5 Hz), 5.29 (m,1H), 4.38 (m,2H), 4.17 (m,1H), 3.80 (m,1H), 3.72 (s,6H), 3.3 (m,4H), 3.14 (m,1H), 2.79 (m,1H), 2.4 (m,1H), 2.15 (m,1H), 1.76 (s,3H). IR (KBR) 3400, 3180, 3055, 2955, 930, 2830, 1690, 1610, 1580, 1510, 1360, 1250, 1180 cm–1. mass spectrum (FAB) 961.66 (M+H), calcd for C48H48N8O12S+H 961.07.

To a solution of 102 mg of (DMTO)$A^{Bz}$sT(OH) in 5 ml of acetonitrile was added 0.22 ml of dichloroacetic acid. The orange solution was stirred at RT for 15 min. After pouring the reaction into one half saturated bicarbonate, the product was extracted with EtOAc (2×40ml). The combined organic layers were washed with brine, dried, and evap. Purification by chromatography on silica (1 to 10% methanol/DCM) gave 68 mg of (HO)$A^{Bz}$sT(OH): NMR (300 MHz, d6-DMSO) δ11.33 (br,1H), 11.26 (br,1H), 8.77 (s,1H), 8.70 (s,1H), 8.47 (br,1H), 8.06 (d,2H,J=8 Hz), 7.66 (t,1H,J=8 Hz), 7.59 (s,1H), 7.55 (d,2H,J=8 Hz), 6.52 (t,1H,J=7 Hz), 6.18 (t,1H,J=7 Hz), 5.41 (d,1H,J=5 Hz), 5.32 (t,1H,J=5 Hz), 5.23 (m,1H), 4.25 (m,1H), 4.19 (m,1H), 3.82 (m,1H), 3.65 (m,2H), 3.0–3.3 (m,3H), 2.78 (m,1H), 2.0–2.3 (m,2H), 1.79 (s,3H). IR (KBr) 3420, 1690, 1620, 1585, 1360, 1175 cm–1. mass spectrum (FAB) meas. 659.23 (M+H), calcd for C27H30N8O10S+H: 659.19.

A slurry of 31 mg of (HO)$A^{Bz}$sT(OH) in 3 ml of methanol was saturated at RT with ammonia gas. The reaction was sealed and heated to 55° C. for 4 hr. The solvent was evap. Purification by chromatography on silica (methanol/DCM gradient) gave 19 mg of d(AsT): NMR (300 MHz, d6-DMSO) δ [partial spectrum] 8.34 (s,1H), 8.14 (s,1H), 7.35 (s,1H), 7.41 (br,2H), 6.37 (dd,1H,J=9,6 Hz), 6.17 (t,1H,J=7 Hz), 5.67 (br,1H), 5.39 (d,1H,J=5 Hz), 5.18 (m,1H), 4.2 (m,2H), 3.81 (m,1H), 3,63 (m,2H), 3.19 (m,1H), 3.01 (m,1H), 2.66 (m,1H), 2.18 (m,1H), 1.78 (s,3H).

Example 8

Preparation of a Sulfamate Ester linked dA-Nucleoside Dimer d(AsA)

A mixture of 57 mg (0.10 mmol) of the compound from Example 1, 65 mg (0.10 mmol) and N6-benzoyl-5'-dimethoxytrityl-2'-deoxyadenosine (Aldrich) in 0.5 ml of acetonitrile was stirred at RT under nitrogen. Triethylamine 0.028 ml (0.2 mmol) was added and the reaction was stirred for 20 hr. After evaporation of the mixture and purification on silica (1–3% methanol/DCM) 87 mg of the fully protected dimer, (DMTO)$A^{Bz}$s$A^{Bz}$(OTBDMS), were obtained: NMR [partial spectrum] (300 MHz,d6-DMSO) δ11.23 (br, 2H), 8.66 (s,1H), 8.65 (s,1H), 8.58 (s,1H), 8.56 (s,1H), 8.56 (br,1H), 8.04 (d,4H,J=8 Hz), 7.5–7.7 (m,6H), 7.15–7.35 (m,9H), 6.77 (dd,4H,J=8,6 Hz), 6.53 (t,1H,J=7 Hz), 6.47 (t,1H,J=7 Hz), 5.27 (m,1H), 4.64 (m,1H), 4.34 (m,1H), 4.01 (m,1H), 3.68 (s,6H), 3.02 (m,1H), 2.78 (m,1H), 2.36 (m,1H), 0.91 (s,9H), 0.15 (s,6H).

51 mg of (DMTO)$A^{Bz}$s$A^{Bz}$(OTBDMS) were treated under nitrogen with a total of 1.5 ml of 1M tetra-n-butylammonium fluoride in THF added in three aliquots over 1 hr intervals. The reaction was stirred at RT for 1 hr. after the final addition of the fluoride reagent. The reaction was partitioned between 1M sodium dihydrogen phosphate and EtOAc. The organic layer was washed with brine, dried, and evap. Purification by column chromatography on silica (1–6% methanol/DCM) gave 36 mg of pure (DMTO) d($A^{Bz}$s$A^{Bz}$) (OH): NMR (300 MHz, d6-DMSO) δ 11.22 (br,2H), 8.67 (s,1H), 8.65 (s,1H), 8.58 (br,2H), 8.54 (br,1H), 8.05 (d,4H,J=7 Hz), 7.5–7.7 (m,6H), 7.33 (m,2H), 7.2 (m,7H), 6.79 (dd,4H,J=7 Hz), 6.52 (t,1H,J=7 Hz), 6.47 (t,1H,J=7 Hz), 5.53 (d,1H,J=5 Hz), 5.37 (m,1H), 4.45 (m,1H) 4.34 (m,1H), 4.01 (m,1H), 3.69 (s,6H), 3.1–3.5 (m,5H(est.)), 2.7–2.95 (m,2H), 2.38 (m,1H).

Treated 21 mg of (DMTO) ($A^{Bz}$s$A^{Bz}$) (OH) with 3 ml of saturated NH3/MeOH in a sealed vial for 3 days at RT. The solvent was evaporated and the residue was stirred with 1 ml of 80% HOAc/water at RT for 45 min. The solvent was removed using a vacuum pump/rotovap and a water bath at RT. Pure d(AsA) was obtained by HPLC: C8 Rainin 10×25 cm column (with guard), gradient=10–60% MeOH/water (linear), flow=3.5 ml/min, sample dissolved in 20% MeOH/water, 6c eluted at 21.2 min. NMR [partial spectrum] (300 MHz,d4-MeOH, all chemical shifts relative to MeOH @ 3.30) δ8.23 (s,1H), 8.20 (s,1H), 8.19 (s,1H), 8.11 (s,1H), 6.37 (m,2H), 5.22 (d,1H,J=6 Hz), 4.59 (m,1H), 4.33 (m,1H), 4.16 (dd,1H,J=7,4 Hz), 3.74 (dq,2H,J=13,3 Hz), 3.47 (m,2H), 2.85–3.0 (m,2H), 2.69 (ddd,1H,J=13,6,1.5 Hz), 2.37 (ddd,1H,J=13,6,3 Hz).

Example 9

Preparation of an Oligonucleotide with a Sulfamate Linked to the 2' or 3' position of a ribonucleoside [((Ph)3CO)[rU]sT(OTBDMS)].

To a solution of 200 mg of 5'-trityluridine (Sigma, St. Louis, Mo.) and 189 mg of 3'-O-t-butyldimethylsilyl-5'-sulfamoylazido-5'-deoxythymidine (from Example 4) in 2.5 ml of anhydrous acetonitrile under nitrogen was added 0.11 ml of triethylamine. After stirring at RT for 20 hr., the solvent was evaporated, and the residue was purified by chromatography on silica (1 to 7% methanol/DCM) giving 81 mg of the major product as one spot on TLC. Analytical HPLC shows a 50:50 mixture of products. Prep HPLC (C8 10×250 mm column with guard (Rainin), gradient: 80–90% over 25 min. of methanol/0.1M triethylammonium bicarbonate, flow=4 ml/min, sample: 10–15 mg/injection) afforded pure ((Ph) 3CO) [rU]sT(OTBDMS) (2' linked) and pure ((Ph)3CO)[rU]sT(OTBDMS) (3' linked). 2' linked: retention time=16.61 min.; NMR (300 MHz,d6-DMSO) δ11.47 (br,1H), 11.34 (br,1H), 8.39 (br,1H), 7.69 (d,1H,J=8 Hz), 7.25–7.4 (m,15H), 6.15 (dd,1H,J=7,6 Hz), 5.93 (d,1H, J=4 Hz ), 5.71 (m,1H), 5.49 (d,1H,J=8 Hz), 5.01 (m,1H), 4.42 (m,1H), 4.36 (m,1H), 3.99 (m,1H), 3.78 (m,1 H), 3.23 (m,2H), 2.25 (m,1H), 2.03 (m,1H), 1.77 (s,3H), 0.87 (s,9H), 0.09 (s,6H). 3' linked: ret. time=18.15 min.; NMR (300 MHz, d6-DMSO) δ 11.46 (br,1H), 11.33 (br,1H), 8.37 (br,1H), 7.65 (d,1H,J=9 Hz), 7.35–7.5 (m,16 H), 6.13 (dd, 1H,J=8,6 Hz), 6.07 (br,1H), 5.79 (d,1H,J=6 Hz), 4.87 (m,1H), 4.47 (m,1H), 4.34 (m,1H), 4.29 (m,1H), 3.80 (m,1H), 3.1–3.4 (m,7H), 2.24 (m,1H), 2.03 (m,1H), 1.76 (s,1H), 0.87 (s,9H), 0.08 (s,6H).

Example 10

Preparation of Sulfamate Ester Linked Block Dimer Phosphoramidite
[(DMTO)A$^{Bz}$sT(OP(OCH$_2$CH$_2$CN)N(iPr$_2$))]

After dissolving 294 mg of (DMTO)A$^{Bz}$sT(OH) in 3 ml of dry DCM, 116 ul of 2-cyanoethyl N,N,N',N'-tetraisopropylphosphorodiamidite (Aldrich, Milwaukee, Wis.) and 31 mg of diisopropylammonium tetrazolide salt (prepared by mixing equal amounts of tetrazole and diisopropylamine) were added and the mixture was stirred for 1 hr. The reaction not complete by TLC (10% methanol/DCM). Another 60 ul of 4d and 15 mg of the tetrazole salt were added and stirring was continued for another 1 hr. The reaction was partitioned between half saturated bicarbonate and EtOAc. The organic layer was washed with brine, dried, and evap. The product was chrom. on silica (1–5% methanol/DCM with 0.5% pyridine) giving 452 mg of semi-pure (DMTO)A$^{Bz}$sT(OP(OCH$_2$CH$_2$CN)N(iPr$_2$)). This material was dissolved in 3 ml of DCM and added this to 150 ml of pentane at −78° C. with stirring. The precipitate was filtered and collected. Repeated this procedure once. The white solid was evaporated from dry pyridine (2x) followed by dry toluene. Obtained (DMTO)A$^{Bz}$sT(OP(OCH$_2$CH$_2$CN)N(iPr$_2$)) as white solid (used without furthur purification): $^{31}$P NMR (300 MHz,d6-DMSO) δ151.133 (s), 150.596 (s) (minor impurities at 15–21 ppm); $^1$H NMR (300 MHz,d6-DMSO) δ11.33 (br, 1H), 11.21 (br,1H), 8.58 (s,2H), 8.52 (br,1H), 8.03 (m,2H), 7.1–7.7 (m), 6.80 (m,4H), 6.52 (t,1H,J=7 Hz), 6.15 (t,1H,J=7 Hz), 5.18 (m,1H), 4.46 (m,1H) 4.37 (m,1H), 3.9–4.1 (m), 2.88 (t,2H,J=6Hz), 2.77 (q,2H,J=6 Hz), 2.2 (m,1H), 1.76 (s,3H), 1.17 (m). mass spectrum (FAB) meas. 1161.76 (M+H), calcd. for C57H65N10O13PS+H 1161.43.

Example 11

Preparation of Oligodeoxyribonucleotides with a Single Sulfamate Linkage

The oligodeoxynucleotide $^5$d(GCGTGCATGC[AsT]CGTACG)$^{3'}$(9c) was synthesized on the CODER automated DNA synthesizer on a 1 micromole scale using standard protocols with the block dimer phosphoramidite ((DMTO)A$^{Bz}$sT(OP(OCH$_2$CH$_2$CN)N(iPr$_2$))) (from Example 10) in a 0.1M acetonitrile solution placed on the X port. The oligomer was cleaved from the solid support using 27% ammonium hydroxide with slow elution over 1 hr. This solution was put in a sealed vial and heated to 55° C. for 4 hr. After evaporation on a rotary evaporator, the crude product was purified by HPLC (C8 column, 10 mm×25 cm) using a linear gradient of 5–15% acetonitrile/0.1M triethylammonium acetate (TEAA). The oily product was evaporated from 50% ethanol/water until a white powder was obtained. The purified product had a retention time of 9.00 min. (C8 analytical 10 cm column, 1.0ml/min, 5–20% CH3CN/0.1M TEAA over 15 min.). A stock solution containing 5.0 ODs 9c/ml water (sterile) was prepared and stored in the freezer.

Example 12

Annealing of a Pair of Oligodeoxyribonucleotides with Single Sulfamate Linkages

The buffer used was pH7.00, 10 mM aqueous sodium phosphate, containing 200 mM sodium chloride and 0.1 mM EDTA. The reference cells contained this buffer. Complementary strands (1.5 μM each) were allowed to anneal 15° C. and then the UV absorption at 260 nm was measured as the temperature was raised to 75° C. (0.4° C./min). The resulting melting curves are shown in FIG. 1. Solid diamonds show data from the oligonucleotide pair 9a:9c (estimated T$_m$=68° C.) and the open squares show data from the oligonucleotide pair 9b:9d (estimatedT$_m$=72° C.). [See below for oligonucleotide sequences 9a, 9b, and 9d.]

Example 13

Figure 2A:
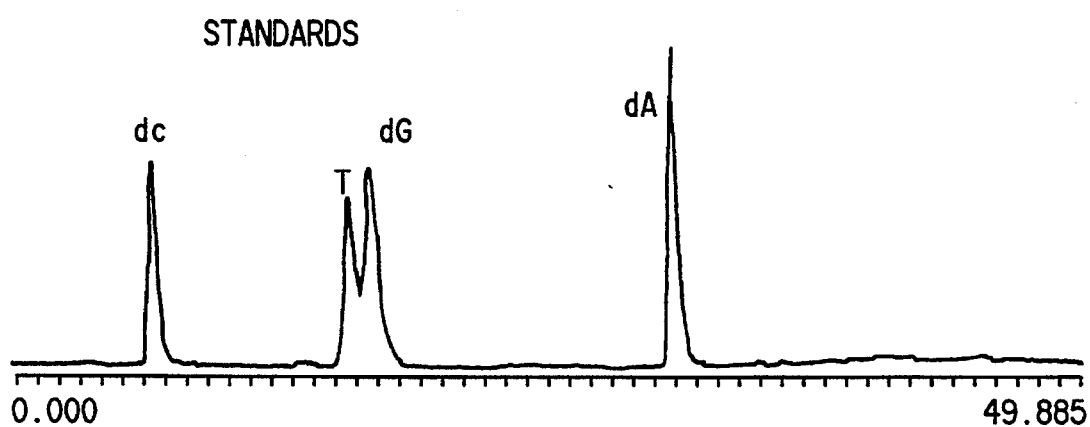
FIG. 2a shows an HPLC chromatogram of a standard mixture of dC, T, dG, and dA.
Figure 2B:
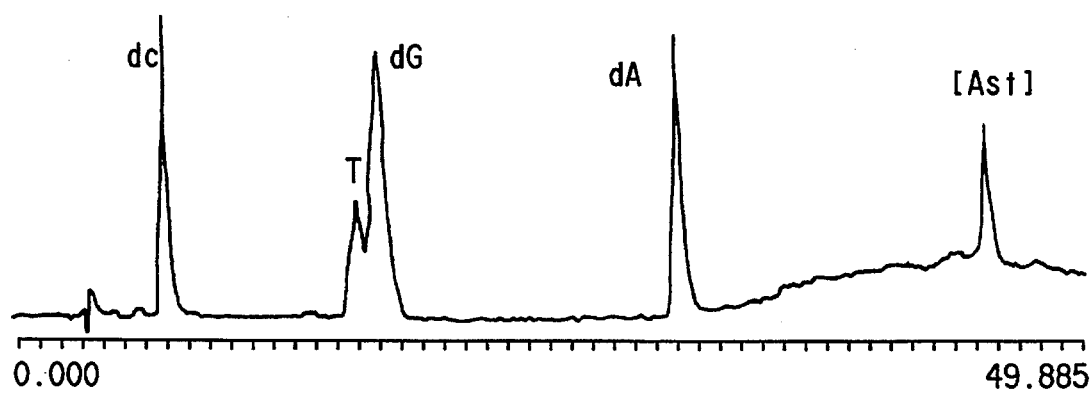
FIG. 2b shows an HPLC chromatogram of the product mixture resulting from prolonged digestion: of oligodeoxynucleotide 9 c. The HPLC conditions used were as follows: C18 Rainin analytical column (4.6 mm×25 cm) with guard, flow of 1.0 ml/min, and a gradient of 10% water/methanol (solvent B) in 50 mM $KH_2PO_4$/water (solvent A) of 0-20 min=3.0% sol.B/sol.A), 20–40 min=3–40% sol.B/sol.A (linear), 40–45 min=40% sol.B/sol.A.

Demonstration of the Exonuclease Resistance of an Oligodeoxyribonucleotide with a Single Sulfamate Linkage The enzyme stock solutions used were 1.8 Units/ml of SVP, (phosphodiesterase I, Sigma, St. Louis, Mo.) and 147 Units/ml of AP (alkaline phosphatase, Sigma, St. Louis, Mo.). The buffer solutions used were tris (100 mM, pH 9) and MgCl$_2$ (50 mM). The digestion was carried out in a 1.5 ml eppendorf tubes by incubating 0.1 Abs. units of the compound from example 14 with 25.6 ul of tris buffer, 24 ul of MgCl$_2$ buffer, 10 ul of SVP stock solution, and 13.6 ul of AP stock solution at 37° for 18 hr. Next 10 ul of 2.5M sodium acetate was added followed by 250 ul of ethanol. After chilling to −78° for 30 min and centrifuging (12K rpm, 10 min), the supernatant was diluted to 1 ml with ethanol and respun. The supernatant was collected and evaporated on a speed-vac. The residue was redissolved in 1.0 ml of sterile water, and was stored at 4° until analyzed. FIG. 2a shows an HPLC chromatogram of a standard mixture of dC, T, dG, and dA. FIG. 2b shows an HPLC chromatogram of the product mixture resulting from prolonged digestion of oligodeoxynucleotide 9c. It can be seen that when the ODN containing the sulfamate ester linkage is digested for an extended length of time, the block dimer emerges intact. An HPLC chromatogram of a sample of the totally deprotected block dimer, d(AsT), which was independently synthesized (see example 19), confirmed that the peak labled as [AsT] had the same retention time as the synthetic material. This demonstrates that the sulfamate ester linkage is extremely resistant to exonucleases.

Example 14

Demonstration Of the Endonuclease Resistance of Duplexes from Oligodeoxyribonucleotides with Single Sulfamate Linkages The oligonucleotide 9a was synthesized as described in Example 11 for 9c. Oligonucleotides 9b and 9d were synthesized by standard methods well known to those skilled in the art. The additional sequences are:

9a $^5$d(CGTACGATGC[AsT]GCACGC)$^{3'}$

9b $^5$d(CGTACGATGCATGCACGC)$^{3'}$

9d $^5$d(GCGTGCATGCATCGTACG)$^{3'}$

Each of the four oligomer strands 9a–9d (10–100 pmol ends) were 5'-end-labelled using T4 polynucleotide kinase (10 units) with γ-$^{32}$P ATP(3000 Ci/mmol). Strands were purified by phenol:chloroform extraction, chloroform extraction, ether extraction and two successive ethanol precipitations. Excess ATP was removed using a NACS PrePac column following the standard protocol (BRL, Bethesda, Md.).

Figure 3:
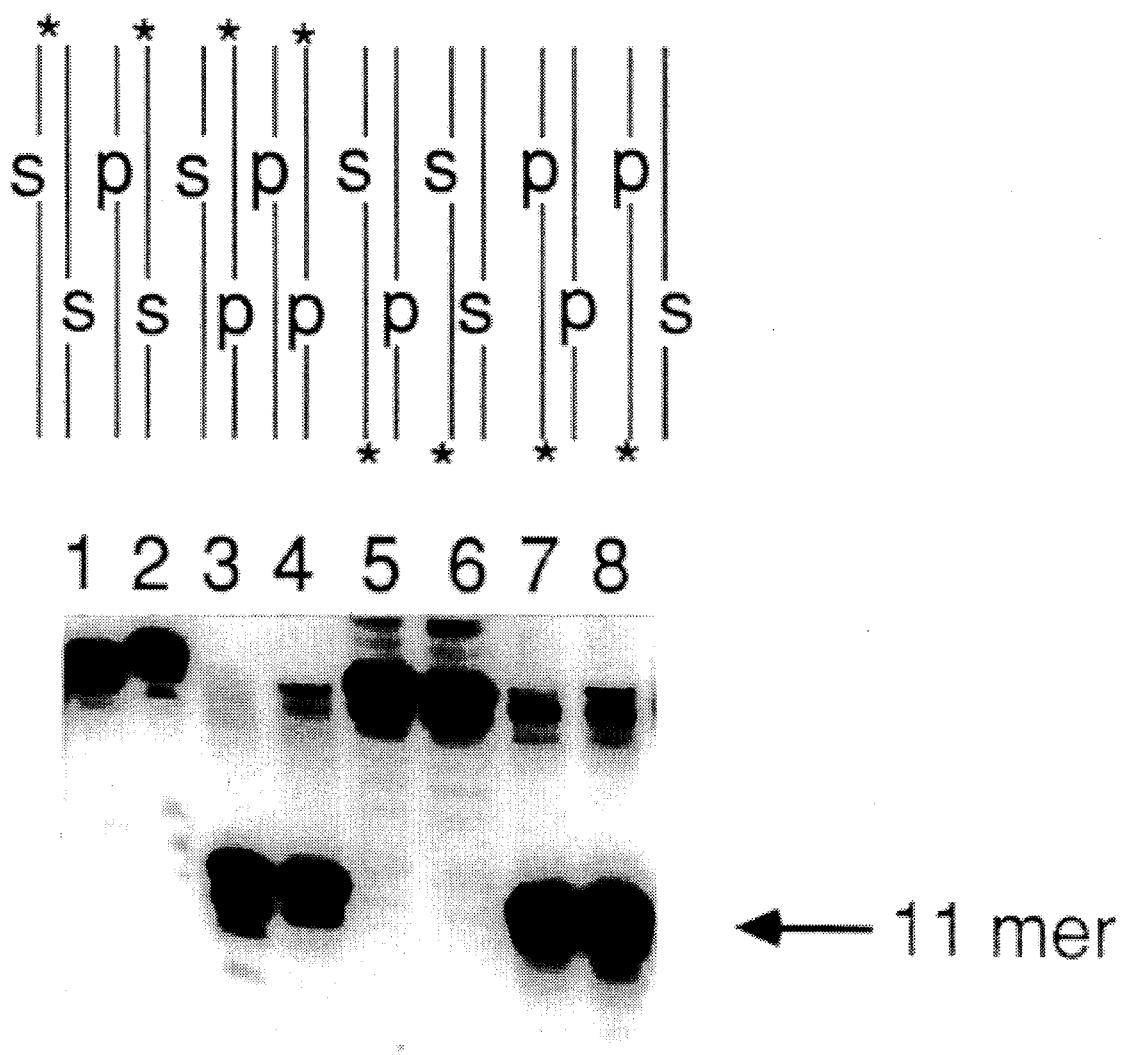
FIG. 3. This figure is a photograph of an autoradiogram of a 20% denaturing polyacrylamide gel illustrating cleavage of sulfamate or phosphate linked oligonucleotides by Nsi I.

The 5'-endlabelled single-stranded oligomers (12,000 cpm , ~1 pmol) were annealed to their unlabelled complements (10 pmol) in 11 μl of buffer containing 50 mM tris-HCl (pH 8.0), 10 mM MgCl$_2$ and 100 mM NaCl. The mixture was heated to 80° C. for 15 min and then cooled slowly to room temperature for 60 min. Restriction endonuclease Nsi I(10 units in 1 μl ) and 7 μl of enzyme reaction buffer was added to each of the annealed samples. The duplex DNA and Nsi I mixtures were placed at 37° C. for 60 min. The samples were ethanol precipitated with the addition of 10 μl of 7.5M ammonium acetate, 1 μl of tRNA and 90 μl of 100 % ethanol. Samples were centrifuged 15 min at 14,000 rpm at room temperature, supernatent liquid was removed and the DNA pellets were dried in vacuo. Samples were resuspended in 3 μl of formamide dye containing 80% deionized formamide, 0.1% xylene cyanol and 0.1% bromophenol blue, and were loaded onto a 20% denaturing polyacrylamide gel. Samples were electrophoresed for two hours at 2000 V. Gel was exposed to Kodak XAR film for 8–24 hours at −70° C. The results are shown in FIG. 3. Lanes 1 and 2 contain strand 9a annealed to strands 9c and 9d respectively; lanes 3 and 4 contain strand 9b annealed to strands 9c and 9d respectively; lanes 5 and 6 contain strand 9c annealed to strands 9b and 9a respectively; lanes 7 and 8 contain strand 9d annealed to strands 9b and 9a respectively. —S— the sulfamate linkage and —P— indicates the phosphodiester linkage.

Example 15

Annealing of a Sulfamate Linked A-Nucleoside Dimer with PolyU

Figure 4:
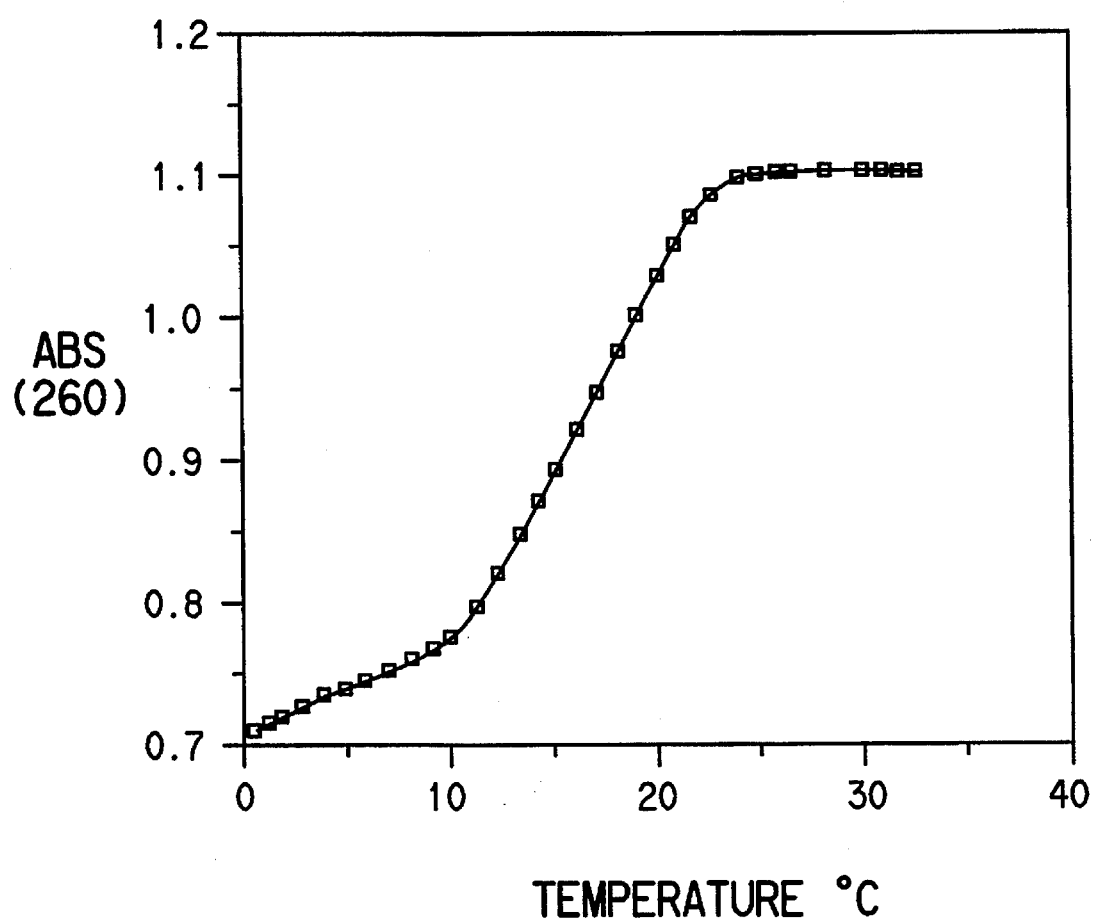
FIG. 4. Demonstrates the meltings profile of d(AsA) vs. poly-uridine in a buffer of 10 mM magnesium H at pH 7.5.

The buffer used was 10 mM in magnesium chloride and Tris (base), and was adjusted to pH 7.5 with 0.1M HCl. The reference cell contained this buffer. The sample cell contained 0.660 OD units of poly U (Sigma, St. Louis, Mo.) and 0.330 OD units of d-AsA in 1.00 ml of buffer. The cells were equilibrated at 0.6° C. for 1 hour, and the temperature was ramped at 1° C./min. The melting profile is shown in FIG. 4. The Tm is estimated to be 15°–18° C. with a hypochromic effect of 35%. The reported literature value for the corresponding natural phosphodiester dimer, d-ApA, is 7.6° C.[25]. This example demonstrates that oligodeoxynucleotides containing only sulfamate linkage(s) can hybridize to their complementary unmodified counterparts and that the hybrid can have greater stability.

Example 16

Demonstration of the stability of the Sulfamate when Linked to the 2' or 3' position of a ribonucleotide A solution of 1 mg of 3' linked ((Ph)3CO) [rU]-sT(OTBDMS) (from Example 9) in 3 ml of 27% ammonium hydroxide was incubated in a sealed vial at RT for 24 hr. The solvent was evap. When the residue was analysized by HPLC (C18 Rainin analytical column (4.6 mm×25 cm) with guard, flow of 1.5 ml/min, and a linear gradient of 80–90% methanol/water over 15 min.) none of the peak at 12.375 min. had converted to the 2'-linked ((Ph)3CO) [rU]sT(OTBDMS) (ret. time 11.110 min.). When a 1 mg sample of the 2' linked ((Ph)3CO) [rU]sT(OTBDMS) was treated in a similar manner, no equilibration was seen either. This demonstrates that sulfamate linked oligoribonucleotide derivatives are base stable with respect to cleavage and migration.

1. G. Zon, *Pharmaceut. Res.*, 5, 539–549 (1988).
2. P. S. Miller and P.O.P.Ts'O, in *Ann. Rep. Med. Chem.*, No. 23, Vinick, ed., p. 295–304, Academic Press, New York (1988).
3. "Antisense RNA and DNA", Current *Communications in Molecular Biology* series, Cold Spring Harbor Press, Cold Spring Harbor (1988).
4. H. E. Moser and P. B. Dervan, *Science*, 238, 645–650 (1987).
5. C. Cazenave, N. Loreau, N. T. Thuong, J. -J. Toulme, and C. Helene, *Nucl. Acids Res.*, 15, 4717–4736 (1987).
6. U. Pieles and U. Englisch, *Nucl. Acids. Res.*, 17, 285–299 (1989).
7. V. V. Vlassov, V. F. Zarytova, I. V. Kitiavin, S. V. Mamaev, and M. A. Podyminogin, *Nucl. Acids. Res.*, 14, 4065–4076 (1986).
8. B. C. F. Chu and L. E. Orgel, Proc. *Nat. Acad. Sci. USA*, 82, 963–967 (1985).
9. C. B. Chen and D. S. Sigman, *J. Amer. Chem. Soc.*, 110, 6570–6572 (1988).
10. F. Morvan, B. Rayner, J. -L. Imbach, S. Thenet, J. -R. Bertrand, J. Paoletti, C. Malvy, and C. Paoletti, *Nucl. Acids Res.*, 15, 3421–3437 (1987).
11. M. Weinfeld and D. C. Livingston, Biochem., 25, 5083–5091 (1986).
12. H. M. Moody, M. H. P. van Genederen, L. H. Koole, H. J. M. Kocken, E. M. Meijer, and H. M. Buck, *Nucl. Acids Res.*, 17, 4769–4782 (1989).
13. M. Matsukura, K. Shinozuka, G. Zon, H. Mitsuya, M. Reitz, J. S. Cohen, and S. Broder, *Proc. Nat. Acad. Sci. USA*, 84, 7706–7710 (1987).
14. P. J. Furdon, Z. Dominski, and R. Kole, *Nucl. Acids. Res.*, 17, 9193–9204 (1989).
15. W. K. -D. Brill, J. -Y. Tang, Y. -X. Ma, and M. H. Caruthers, *J. Amer. Chem. Soc.*, 111, 2321–2322 (1989).
16. J. M. Coull, D. V. Carlson, and H. L. Weith, *Tet. Lett.*, 28, 745–748 (1987).
17. E. P. Stirchak, J. E. Summerton, and D. D. Weller, *J. Org. Chem.*, 52, 4202–4206 (1987).
18. S. Agrawal, J. Goodchild, M. P. Civeira, A. H. Thronton, P. S. Sarin, and P. C. Zamecnik, *Proc. Nat. Acad. Sci. USA*, 85, 7079–7083 (1988).
19. M. H. Caruthers, W. K -D. Brill, Y. -X. Ma, W. S. Marshall, J. Nielsen, H. Sasmor, and J. -Y. Tang, J. Cell. Biochem., Supp. 13D, 17 (1989).
20. Poster presented by C. Blonski at Conference on "Recognition Studies in Nucleic Acids", Sheffield, England, Apr. 16–21, 1989.
21. D. A. Shuman, R. K. Robins, and M. J. Robins, *J. Amer. Chem. Soc.*, 91, 3391–3392 (1969).
22. G. R. Gough, D. N. Nobbs, J. C. Middleton, F. Penglis-Caredes, and M. H. Maguire, *J. Med. Chem.*, 21, 520–525 (1978).
23. K. Isono, M. Uramoto, H. Kusakabe, N. Miyata, T. Koyama, M. Ubukata, S. K. Sethi, and J. A. McCloskey, *J. Antiblot.*, 37, 670–672 (1984).
24. M. Ubukata and K. Isono, *Tet. Lett.*, 27, 3907–3908 (1986).
25. P. S. Miller, K. N. Fang, N. S. Kondo, and P. O. P. Ts'o, *J. Amer. Chem. Soc.*, 93, 6657–6665 (1971).
26. Charachon, G., Sobol, R. W. Bisbal, C., Salehzada, T., Silhol, M., Charubula, R., Pfleiderer, W., Lebleu, B. & Suhadolnik, *Biochemistry*, 29, 2550–2555 (1990).
27. Zamecnik, P. R., Goodchild, J., Taguchi, Y. and Sarin, P. S., *Proc. Natl. Acad. Sci. , USA*, 83, (1986) pp. 1028–1032.
28. Harel-Bellan, A. Ferris, D. K., Vinocour, M., Holt, J. T., and Farrar, W. L., *J. Immunol.*, 140, (1988) 2431–2435.

29. Walder, R. Y., and Walder, J. A., (1988) *Proc. Natl. Acad. Sci. USA*, 85, (1988), 5011–5015.
30. Principles of Nucleic Acid Structures, (1984) Springer-Verlag, New York, pp. 51–104, 159–200.
31. Lamaitre, M., Bayard, B. and Leblew, B. (1987) *Proc. Natl. Acad. Sci. USA*, 84, 648–652.
32. "Oligodeoxynucleotides: Antisense Inhibitors of Gene Experssion", *Topics in Molecular and Structural Biology* series, CRC Press Inc., Boca Raton, Fla. (1989).
33. S. Benner, WO 89/12060.
34. P. S. Miller, J. Yano, E. Yano, C. Carroll, K. Joyaraman, and P. Tso, *Biochem.*, 18, 5134–5143 (1979).
35. R. B. Waring, *Nucl. Acids Res.*, 17, 10281–10293 (1989).
36. I. Yamamoto, M. Sekine, and T. Hata, *J. Chem. Soc., Perkin Trans.* 1, 306–310 (1980).
37. Charubala, Uhlmann, Beter, and Pfleiderer, *Synthesis*, 965 (1984).
38. T. -S. Lin, *J. Pharm. Sci.*, 73, 1568–1570 (1984).
39. *Oligonucleotide Synthesis: A Practical Approach*, Ed. by M. J. Gait, IRL Press Ltd., Washington, D.C. (1984).

All references are incorporated herein.

What is claimed is:

1. A compound of the formula:

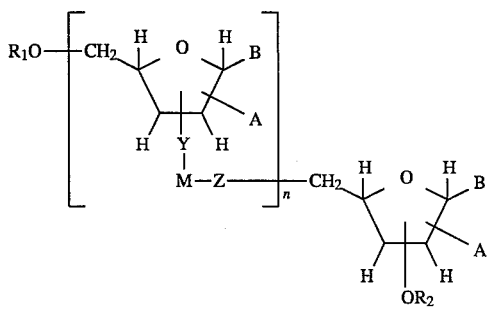

wherein:

A is H, OH, OR$_8$, OQ or halogen;

B is a naturally occurring nucleic acid base or modified nucleic acid base;

Y is —N(R)— or O;

Z is —N(R$_7$)— or O;

wherein Y, OR$_2$, and A are independently bonded to the 2' or 3' position and provided further that A is bonded to a position different from that of Y or OR$_2$;

wherein each M is independently selected from

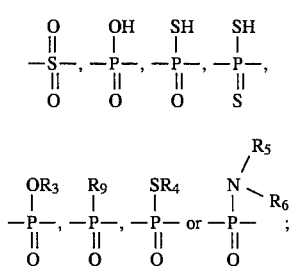

provided at least one M is S(=O)=O; and provided that when M is S(=O)=O, Y and Z cannot both be O;

n is 1 to 75;

R is H or alkyl of 1 to 6 carbon atoms;

R$_1$ is H$_2$PO$_3$, H$_3$P$_2$O$_5$, H$_4$P$_3$O$_7$ and their suitable salts, H or an hydroxyl protecting group;

R$_2$ is H$_2$PO$_3$, H$_3$P$_2$O$_5$, H$_4$P$_3$O$_7$ and their suitable salts, H or an hydroxyl protecting group;

R$_3$ is alkyl or cyanoethyl;

R$_4$ is H or alkyl of 1 to 6 carbon atoms;

R$_5$ is H or alkyl of 1 to 6 carbon atoms;

R$_6$ is H or alkyl of 1 to 6 carbon atoms;

R$_7$ is H or alkyl of 1 to 6 carbon atoms;

R$_8$ is alkyl of 1 to 6 carbon atoms;

R$_9$ is alkyl of 1 to 6 carbon atoms or cyanoethyl; and

Q is an hydroxyl protecting group;
provided that when each M is S(=O)=O, then at least one B group is not thymine.

2. The compound of claim 1 wherein when M is S(=O)=O, one of Y or Z is —N(R)— or —N(R$_7$)— and R or R$_7$ is H.

3. The compound of claim 1 wherein R is an alkyl of less than 5 carbon atoms.

4. The compound of claim 1 wherein R$_3$ is an alkyl of less than 5 carbon atoms.

5. The compound of claim 1 wherein R$_4$ is an alkyl of less than 5 carbon atoms.

6. The compound of claim 1 wherein R$_5$ is an alkyl of less than 5 carbon atoms.

7. The compound of claim 1 wherein R$_6$ is an alkyl of less than 5 carbon atoms.

8. The compound of claim 1 wherein R$_7$ is an alkyl of less than 5 carbon atoms.

9. The compound of claim 1 wherein R$_8$ is an alkyl of less than 5 carbon atoms.

10. The compound of claim 1 wherein R$_9$ is an alkyl of less than 5 carbon atoms.

11. The compound of claim 1 wherein the A substituent is in the 2'-position.

12. The compound of claim 1 wherein A is selected from the group consisting of H and OH.

13. The compound of claim 1 wherein B is adenine, guanine, cytosine, thymine or uracil.

14. The compound of claim 1 wherein M is S(=O)=O for the internucleotide linkage at the 3' terminus or 5' terminus, or both the 3' terminus and the 5' terminus of the compound.

15. The compound of claim 1 wherein M is S(=O)=O.

16. The compound of claim 1 wherein M is S(=O)=O or P(=O)—OH.

17. The compound of claim 16 wherein Y or Z is —N(R)— or —N(R$_7$)—, and R or R$_7$ is H.

18. A compound of the formula:

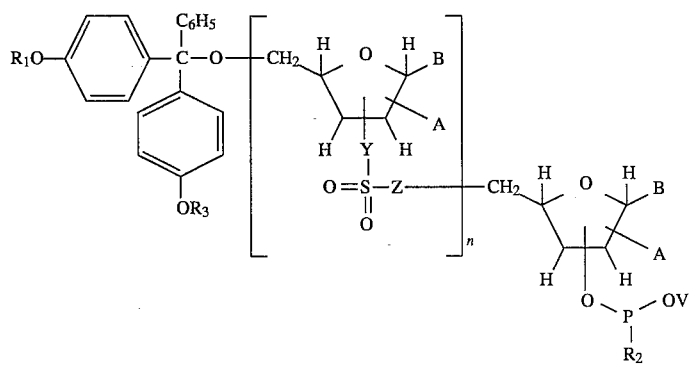

wherein:
- A is H, OH, OR$_4$, OQ, or halogen;
- B is a naturally occurring nucleic acid base or modified nucleic acid base;
- n is 1 to 75;
- R$_1$ is alkyl of 1 to 6 carbon atoms;
- R$_2$ is dialkylamino, morpholino, piperidino, or pyrrolidono;
- R$_3$ is alkyl of 1 to 6 carbon atoms;
- R$_4$ is alkyl of 1 to 6 carbon atoms;
- Y is —N(R)— or O;
- Z is —N(R)— or O;
- wherein Y, OP(R$_2$)(OV), and A are independently bonded to the 2' or 3' position and provided further that A is bonded to a position different from that of Y or OP(R$_2$)(OV);
- R is H or alkyl of 1 to 6 carbon atoms;
- Q is an hydroxyl protecting group; and
- V is an hydroxyl protecting group;

provided that at least one B group is not thymine.

19. The compound of claim 18 wherein V is cyanoethyl or methyl.

20. The compound of claim 18 wherein Q is selected from the group consisting of C$_1$–C$_5$ trialkylsilyl, C$_1$–C$_5$ alkyl, acyl, cyanoethyl or tetrahydropyran.

21. The compound of claim 18 wherein R is an alkyl of less than 5 carbon atoms.

22. The compound of claim 18 wherein R$_1$ is an alkyl of less than 5 carbon atoms.

23. The compound of claim 18 wherein R$_3$ is an alkyl of less than 5 carbon atoms.

24. The compound of claim 18 wherein R$_4$ is an alkyl or less than 5 carbon atoms.

* * * * *